US009759729B2

(12) United States Patent
Sylvester et al.

(10) Patent No.: US 9,759,729 B2
(45) Date of Patent: Sep. 12, 2017

(54) BLOOD BIOMARKERS FOR NECROTIZING ENTEROCOLITIS

(71) Applicant: The Board of Trustees of the Leland Stanford Junior University, Palo Alto, CA (US)

(72) Inventors: Karl G. Sylvester, Los Altos, CA (US); Guozhong Tao, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 235 days.

(21) Appl. No.: 14/406,098

(22) PCT Filed: Jun. 10, 2013

(86) PCT No.: PCT/US2013/044995
§ 371 (c)(1),
(2) Date: Dec. 5, 2014

(87) PCT Pub. No.: WO2013/185134
PCT Pub. Date: Dec. 12, 2013

(65) Prior Publication Data
US 2015/0126622 A1 May 7, 2015

Related U.S. Application Data

(60) Provisional application No. 61/657,577, filed on Jun. 8, 2012.

(51) Int. Cl.
*G01N 33/68* (2006.01)
(52) U.S. Cl.
CPC ... *G01N 33/6893* (2013.01); *G01N 2333/515* (2013.01); *G01N 2333/75* (2013.01);
(Continued)

(58) Field of Classification Search
None
See application file for complete search history.

(56) References Cited

U.S. PATENT DOCUMENTS

2009/0104605 A1* 4/2009 Siuzdak ............... C12Q 1/6883
435/6.18
2009/0191551 A1 7/2009 Morrow et al.

FOREIGN PATENT DOCUMENTS

WO 2007078841 A2 7/2007

OTHER PUBLICATIONS

Aydemir et al. "Serum intestinal fatty acid binding protein level for early diagnosis and prediction of severity of necrotizing enterocolitis", Early Hum Dev. 87(10):659-61 (2011).
(Continued)

*Primary Examiner* — Robert Xu
(74) *Attorney, Agent, or Firm* — Bret E. Field; Bozicevic, Field & Francis LLP

(57) ABSTRACT

Necrotizing Enterocolitis (NEC) biomarkers, NEC biomarker panels, and methods for obtaining a NEC signature for a sample are provided. Also provided are methods, compositions, and kits for making a Necrotizing Enterocolitis (NEC) assessment of an individual, e.g. for diagnosing NEC in a patient, prognosing NEC in a patient, treating an NEC patient, etc. These methods find use in a number of applications, such as diagnosing and treating infants who are suspected of having NEC, intestinal perforation (IP), or sepsis.

19 Claims, 21 Drawing Sheets

*Study design for discovery of the potential biomarkers of NEC diagnosis*

(52) U.S. Cl.
CPC .............. *G01N 2333/91085* (2013.01); *G01N 2800/067* (2013.01); *G01N 2800/52* (2013.01)

(56) References Cited

OTHER PUBLICATIONS

Bell et al. "Neonatal Necrotizing Enterocolitis Therapeutic Decisions Based Upon Clinical Staging." Annals of Surgery, Jan. 1978, vol. 187, No. 1, pp. 1-7.
Eras et al. "Serum amyloid-A levels in neonatal necrotizing enterocolitis", J. Clin. Lab. Anal. 2011, 25(4):233-7.
Evennett et al. "A systematic review of serologic tests in the diagnosis of necrotizing enterocolitis", J. Pediatr. Surg. 2009, vol. 44, pp. 2192-2201.
Ioannou et al. "Plasma citrulline levels in preterm neonates with necrotizing enterocolitis", Early Hum. Dev. Jan. 31, 2012.
Ng et al. "Host-Response Biomarkers for Diagnosis of Late-Onset Septicemia and Necrotizing Enterocolitis in Preterm Infants", The Journal of Clinical Investigation, 2010, vol. 120, No. 8, pp. 2989-3000.
Tayman et al. "C5a, A Complement Activation Product, Is a Useful Marker in Predicting the Severity of Necrotizing Enterocolitis", Tohoku J. Exp. Med., 2011, vol. 224, pp. 143-50.
Thuijls et al. "Non-Invasive Markers for Early Diagnosis and Determination of the Severity of Necrotizing Enterocolitis", Annals of Surgery, vol. 251, No. 6, Jun. 2010, pp. 1174-1180.
Young et al. "Biomarkers for Infants at Risk for Necrotizing Enterocolitis: Clues to Prevention?" Pediatric Research, vol. 65, No. 5. Pt. 2, 2009, pp. 91R-97R.

* cited by examiner

|  | NEC M | NEC S | Control | SEPSIS | p value |
|---|---|---|---|---|---|
|  | n = 20 (25%) | n = 20(25%) | n = 18 (22.5%) | n = 22 (27.5%) |  |
| Gender* |  |  |  |  | 0.43 |
| M | 8 (44.4%) | 7 (35%) | 8 (36.4%) | 8 (40%) |  |
| F | 10 (55.6%) | 13 (65%) | 14 (63.6%) | 12 (60%) |  |
| Race* |  |  |  |  | 0.011 |
| Asian | 4 (22.2%) | 1 (5%) | 4 (18.2%) | 3 (15%) |  |
| Black | 2 (11.1%) | 9 (45%) | 3 (13.6%) | 0 (0%) |  |
| Native Hawaiian or Pacific Islander | 0 (0%) | 0 (0%) | 0 (0%) | 1 (5%) |  |
| White | 12 (66.7%) | 9 (45%) | 15 (68.2%) | 16 (80%) |  |
| Other | 0 (0%) | 1 (5%) | 0 (%) | 0 (0%) |  |
| Gestational Age (weeks)^ | 28.8 (27.2-30.4) | 26.5 (25.3-27.8) | 32.2 (30.6-33.7) | 30.7 (28.6-32.8) | <0.001 |
| Birth Weight (grams)^ | 1151.5(912.2-1390.8) | 919.0(743.8-1094.1) | 1935.2(1575.3-2295.0) | 1609.2(1186.6-2031.8) | <0.001 |

* Cochran Mantel-Haensezl Chi Square test with adjustment for different institutions is used. N is reported with percentages in parentheses.
^ ANOVA with adjustment for different institutions is used. Least Square Mean is reported with 95% CI in parentheses.

Figure 2

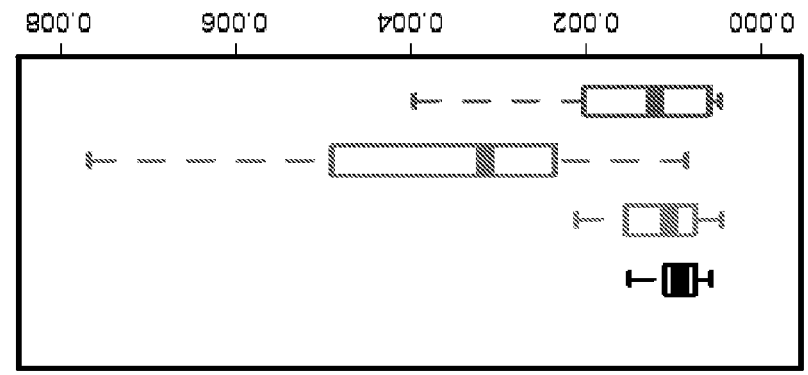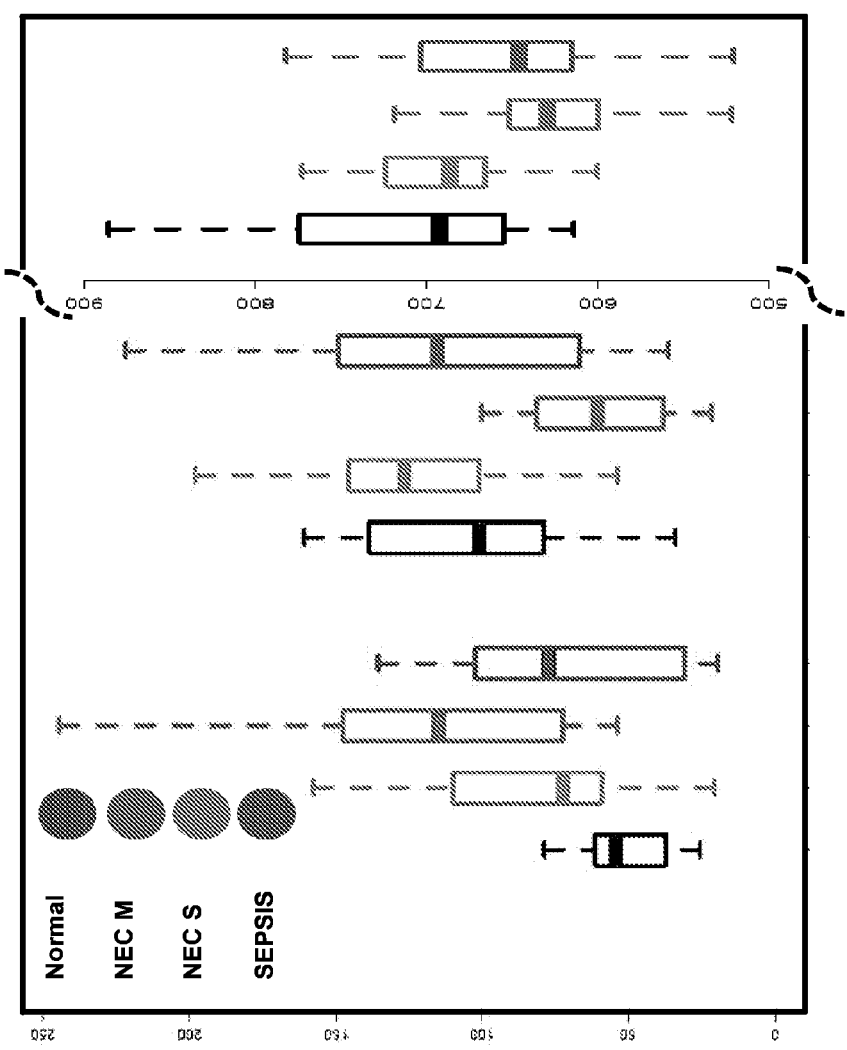
Figure 7

Mann Whitney test P values.

| | NEC M vs. S | NEC M vs. Sepsis | NEC S vs. Sepsis |
|---|---|---|---|
| AGT | 0.03439 | 0.4819 | 0.002961 |
| HPX | 7.27E-05 | 0.4988 | 0.003344 |
| A2M | 6.74E-04 | 0.0398 | 0.2571 |
| Biomarker Panel | 4.51E-05 | 0.8287 | 6.22E-05 |

The AGT human protein sequence is:
MRKRAPQSEMAPAGVSLRATILCLLAWAGLAAGDRVYIHPFHLVIHNESTCEQLAKANA
GKPKDPTFIPAPIQAKTSPVDEKALQDQLVLVAAKLDTEDKLRAAMVGMLANFLGFRIY
GMHSELWGVVHGATVLSPTAVFGTLASLYLGALDHTADRLQAILGVPWKDKNCTSRLD
AHKVLSALQAVQGLLVAQGRADSQAQLLLSTVVGVFTAPGLHLKQPFVQGLALYTPVV
LPRSLDFTELDVAAEKIDRFMQAVTGWKTGCSLMGASVDSTLAFNTYVHFQGKMKGFS
LLAEPQEFWVDNSTSVSVPMLSGMGTFQHWSDIQDNFSVTQVPFTESACLLLIQPHYA
SDLDKVEGLTFQQNSLNWMKKLSPRTIHLTMPQLVLQGSYDLQDLLAQAELPAILHTEL
NLQKLSNDRIRVGEVLNSIFFELEADEREPTESTQQLNKPEVLEVTLNRPFLFAVYDQSA
TALHFLGRVANPLSTA
(SEQ ID NO: 1).

The AGT human nucleic acid sequence is:
atcccatgagcgggcagcagggtcagaagtggccccgtgttgcctaagcaagactctcccctgccctctgccctctgcac
ctccggcctgcatgtccctgtggcctcttgggggtacatctcccggggctgggtcagaaggcctgggtggttggcctcaggct
gtcacacacctagggagatgctcccgtttctgggaaccttggccccgactcctgcaaacttcggtaaatgtgtaactcgacc
ctgcaccggctcactctgttcagcagtgaaactctgcatcgatcactaagacttcctggaagaggtcccagcgtgagtgtcg
cttctggcatctgtccttctggccagcctgtggtctggccaagtgatgtaaccctcctctccagcctgtgcacaggcagcctgg
gaacagctccatccccaccccctcagctataaatagggcatcgtgacccggccgggggaagaagctgccgttgttctgggt
actacagcagaagggtatgcggaagcgagcaccccagtctgagatggctcctgccggtgtgagcctgagggccaccat
cctctgcctcctggcctgggctggcctggctgcaggtgaccgggtgtacatacacccttccacctcgtcatccacaatgag
agtacctgtgagcagctggcaaaggccaatgccgggaagcccaaagaccccaccttcatacctgctccaattcaggcca
agacatcccctgtggatgaaaaggccctacaggaccagctggtgctagtcgctgcaaaacttgacaccgaagacaagtt
gagggccgcaatggtcgggatgctggccaacttcttgggcttccgtatatatggcatgcacagtgagctatggggcgtggtc
catgggggccaccgtcctctcccaacggctgtctttggcaccctggcctctctctatctgggagccttggaccacacagctga
caggctacaggcaatcctgggtgttccttggaaggacaagaactgcacctcccggctggatgcgcacaaggtcctgtctgc
cctgcaggctgtacagggcctgctagtgggcccagggcagggctgatagccaggcccagctgctgctgtccacggtggtgg
gcgtgttcacagccccaggcctgcacctgaagcagccgtttgtgcagggcctggctctctataccctgtggtcctcccacg
ctctctggacttcacagaactggatgttgctgctgagaagattgacaggttcatgcaggctgtgacaggatggaagactggc
tgctccctgatgggagccagtgtggacagcaccctggctttcaacacctacgtccacttccaagggaagatgaagggcttct
ccctgctggccgagccccaggagttctgggtggacaacagcacctcagtgtctgttcccatgctctctggcatgggcaccttc
cagcactggagtgacatccaggacaacttctcggtgactcaagtgcccttcactgagagcgcctgcctgctgctgatccag
cctcactatgcctctgacctggacaaggtggagggtctcacttccagcaaaactccctcaactggatgaagaaactatctc
cccggaccatccacctgaccatgccccaactggtgctgcaaggatcttatgacctgcaggacctgctcgcccaggctgag
ctgcccgccattctgcacaccgagctgaacctgcaaaaattgagcaatgaccgcatcagggtgggggaggtgctgaaca
gcatttttttgagcttgaagcggatgagagagagcccacagagtctacccaacagcttaacaagcctgaggtcttggaggt
gaccctgaaccgcccattcctgtttgctgtgtatgatcaaagcgccactgccctgcacttcctgggccgcgtggccaacccg
ctgagcacagcatgaggccagggccccagaacacagtgcctggcaaggcctctgcccctggcctttgaggcaaaggcc
agcagcagataacaaccccggacaaatcagcgatgtgtcaccccagtctcccacctttcttctaatgagtcgactttgag
ctggaaagcagccgtttctccttggtctaagtgtgctgcatggagtgagcagtagaagcctgcagcggcacaaatgcacct
cccagtttgctgggttatttagagaatgggggtggggaggcaagaaccagtgtttagcgcgggactactgttccaaaaag
aattccaaccgaccagcttgtttgtgaaacaaaaaagtgttcccttttcaagttgagaacaaaaattgggttttaaaattaaag
tatacattttgcattgccttcggtttgtatttagtgtcttgaatgtaagaacatgacctccgtgtagtgtctgtaatacctagtttttc
cacagatgcttgtgattttgaacaatacgtgaaagatgcaagcacctgaatttctgtttgaatgcggaaccatagctggttattt
ctcccttgtgttagtaataaacgtcttgccacaataagcctccaaaaaaaa
(SEQ ID NO: 4).

Figure 16

The HPX human protein sequence is:
MARVLGAPVALGLWSLCWSLAIATPLPPTSAHGNVAEGETKPDPDVTERCSDGWSFD
ATTLDDNGTMLFFKGEFVWKSHKWDRELISERWKNFPSPVDAAFRQGHNSVFLIKGDK
VWVYPPEKKEKGYPKLLQDEFPGIPSPLDAAVECHRGECQAEGVLFFQGDREWFWDL
ATGTMKERSWPAVGNCSSALRWLGRYYCFQGNQFLRFDPVRGEVPPRYPRDVRDYF
MPCPGRGHGHRNGTGHGNSTHHGPEYMRCSPHLVLSALTSDNHGATYAFSGTHYW
RLDTSRDGWHSWPIAHQWPQGPSAVDAAFSWEEKLYLVQGTQVYVFLTKGGYTLVS
GYPKRLEKEVGTPHGIILDSVDAAFICPGSSRLHIMAGRRLWWLDLKSGAQATWTELP
WPHEKVDGALCMEKSLGPNSCSANGPGLYLIHGPNLYCYSDVEKLNAAKALPQPQNV
TSLLGCTH
(SEQ ID NO: 2).

The HPX human nucleic acid sequence is:
aactctatatagggagttcaactggtcacccagagctgtcctgtggcctctgcagctcagcatggctagggtactgggagca
cccgttgcactggggttgtggagcctatgctggtctctggccattgccaccccctcttcctccgactagtgcccatgggaatgttg
ctgaaggcgagaccaagccagacccagacgtgactaacgctgctcagatggctggagctttgatgctaccaccctgga
tgacaatggaaccatgctgtttttaaaggggagtttgtgtggaagagtcacaaatgggaccgggagttaatctcagagaga
tggaagaatttccccagccctgtggatgctgcattccgtcaaggtcacaacagtgtctttctgatcaaggggggacaaagtctg
ggtatacctcctgaaaagaaggagaaaggatacccaaagttgctccaagatgaatttcctggaatcccatccccactgg
atgcagctgtggaatgtcaccgtggagaatgtcaagctgaaggcgtcctcttcttccaaggtgaccgcgagtggttctggga
cttggctacgggaaccatgaaggagcgttcctggccagctgttgggaactgctcctctgccctgagatggctgggccgctac
tactgcttccagggtaaccaattcctgcgcttcgaccctgtcaggggagaggtgcctcccaggtacccgcgggatgtccga
gactacttcatgccctgccctggcagaggccatggacacaggaatgggactggccatgggaacagtacccaccatggcc
ctgagtatatgcgctgtagcccacatctagtcttgtctgcactgacgtctgacaaccatggtgccacctatgccttcagtggga
cccactactggcgtctggacaccagccgggatggctggcatagctggcccattgctcatcagtggccccagggtccttcag
cagtggatgctgccttttcctgggaagaaaaaactctatctggtccagggcacccaggtatatgtcttcctgacaaagggagg
ctatacccctagtaagcggttatccgaagcggctggagaaggaagtcgggacccctcatgggattatcctggactctgtggat
gcggcctttatctgccctgggtcttctcggctccatatcatggcaggacggcggctgtggtggctggacctgaagtcaggag
cccaagccacgtggacagagcttccttggccccatgagaaggtagacggagccttgtgtatggaaaagtcccttggccct
aactcatgttccgccaatggtcccggcttgtacctcatccatggtcccaatttgtactgctacagtgatgtggagaaactgaat
gcagccaaggcccttccgcaacccagaatgtgaccagtctcctgggctgcactcactgaggggccttctgacatgagtct
ggcctggccccacctcctagttcctcataataaagacagattgcttcttcgcttctcactgaggggccttctgacatgagtctgg
cctggccccacctccccagtttctcataataaagacagattgcttcttcacttgaatcaagggacctaaaaaaaaaaaa
(SEQ ID NO: 5).

Figure 17

The A2M human protein sequence is:
MGKNKLLHPSLVLLLLVLLPTDASVSGKPQYMVLVPSLLHTETTEKGCVLLSYLNETVTV
SASLESVRGNRSLFTDLEAENDVLHCVAFAVPKSSSNEEVMFLTVQVKGPTQEFKKRT
TVMVKNEDSLVFVQTDKSIYKPGQTVKFRVVSMDENFHPLNELIPLVYIQDPKGNRIAQ
WQSFQLEGGLKQFSFPLSSEPFQGSYKVVVQKKSGGRTEHPFTVEEFVLPKFEVQVT
VPKIITILEEEMNVSVCGLYTYGKPVPGHVTVSICRKYSDASDCHGEDSQAFCEKFSGQ
LNSHGCFYQQVKTKVFQLKRKEYEMKLHTEAQIQEEGTVVELTGRQSSEITRTITKLSF
VKVDSHFRQGIPFFGQVRLVDGKGVPIPNKVIFIRGNEANYYSNATTDEHGLVQFSINTT
NVMGTSLTVRVNYKDRSPCYGYQWVSEEHEEAHHTAYLVFSPSKSFVHLEPMSHELP
CGHTQTVQAHYILNGGTLLGLKKLSFYYLIMAKGGIVRTGTHGLLVKQEDMKGHFSISIP
VKSDIAPVARLLIYAVLPTGDVIGDSAKYDVENCLANKVDLSFSPSQSLPASHAHLRVTA
APQSVCALRAVDQSVLLMKPDAELSASSVYNLLPEKDLTGFPGPLNDQDDEDCINRHN
VYINGITYTPVSSTNEKDMYSFLEDMGLKAFTNSKIRKPKMCPQLQQYEMHGPEGLRV
GFYESDVMGRGHARLVHVEEPHTETVRKYFPETWIWDLVVVNSAGVAEVGVTVPDTIT
EWKAGAFCLSEDAGLGISSTASLRAFQPFFVELTMPYSVIRGEAFTLKATVLNYLPKCIR
VSVQLEASPAFLAVPVEKEQAPHCICANGRQTVSWAVTPKSLGNVNFTVSAEALESQE
LCGTEVPSVPEHGRKDTVIKPLLVEPEGLEKETTFNSLLCPSGGEVSEELSLKLPPNVV
EESARASVSVLGDILGSAMQNTQNLLQMPYGCGEQNMVLFAPNIYVLDYLNETQQLTP
EIKSKAIGYLNTGYQRQLNYKHYDGSYSTFGERYGRNQGNTWLTAFVLKTFAQARAYIF
IDEAHITQALIWLSQRQKDNGCFRSSGSLLNNAIKGGVEDEVTLSAYITIALLEIPLTVTHP
VVRNALFCLESAWKTAQEGDHGSHVYTKALLAYAFALAGNQDKRKEVLKSLNEEAVKK
DNSVHWERPQKPKAPVGHFYEPQAPSAEVEMTSYVLLAYLTAQPAPTSEDLTSATNIV
KWITKQQNAQGGFSSTQDTVVALHALSKYGAATFTRTGKAAQVTIQSSGTFSSKFQVD
NNNRLLLQQVSLPELPGEYSMKVTGEGCVYLQTSLKYNILPEKEEFPFALGVQTLPQTC
DEPKAHTSFQISLSVSYTGSRSASNMAIVDVKMVSGFIPLKPTVKMLERSNHVSRTEVS
SNHVLIYLDKVSNQTLSLFFTVLQDVPVRDLKPAIVKVYDYYETDEFAIAEYNAPCSKDL
GNA (SEQ ID NO: 3).

Figure 18

The A2M human nucleic acid sequence is:
gcacacagagcagcataaagcccagttgctttgggaagtgtttgggaccagatggattgtagggagtagggtacaatacagtctgttctc
ctccagctccttcttctgcaacatggggaagaacaaactccttcatccaagtctggttcttctcctcttggtcctcctgcccacagacgcctc
agtctctggaaaaccgcagtatatggttctggtcccctccctgctccacactgagaccactgagaagggctgtgtccttctgagctacctga
atgagacagtgactgtaagtgcttccttggagtctgtcaggggaaacaggagcctcttcactgacctggaggcggagaatgacgtactc
cactgtgtcgccttcgctgtcccaaagtcttcatccaatgaggaggtaatgttcctcactgtccaagtgaaaggaccaacccaagaattta
agaagcggaccacagtgatggttaagaacgaggacagtctggtctttgtccagacagacaaatcaatctacaaaccagggcagaca
gtgaaatttcgtgttgtctccatggatgaaaactttcacccccctgaatgagttgattccactagtatacattcaggatcccaaaggaaatcgc
atcgcacaatggcagagtttccagttagagggtggcctcaagcaattttctttccctctcatcagagcccttccagggctcctacaaggt
ggtggtacagaagaaatcaggtggaaggacagagcacccttcaccgtggaggaatttgttcttcccaagtttgaagtacaagtaacag
tgccaaagataatcaccatcttggaagaagagatgaatgtatcagtgtgtggcctatacacatatgggaagcctgtccctggacatgtga
ctgtgagcatttgcagaaagtatagtgacgcttccgactgccacggtgaagattcacaggctttctgtgagaaattcagtggacagctaaa
cagccatggctgcttctatcagcaagtaaaaaccaaggtcttccagctgaagaggaaggagtatgaaatgaaacttcacactgaggcc
cagatccaagaagaaggaacagtggtggaattgactggaaggcagtccagtgaaatcacaagaaccataaccaaactctcatttgtg
aaagtggactcacactttcgacagggaattcccttctttgggcaggtgcgcctagtagatgggaaaggcgtccctataccaaataaagtc
atattcatcagaggaaatgaagcaaactattactccaatgctaccacggatgagcatggccttgtacagttctctatcaacaccaccaatg
ttatgggtacctctcttactgttagggtcaattacaaggatcgtagtccctgttacggctaccagtgggtgtcagaagaacacgaagaggc
acatcacactgcttatcttgtgttctccccaagcaagagctttgtccaccttgagcccatgtctcatgaactaccctgtggccatactcagac
agtccaggcacattatattctgaatgggaggcaccctgctggggctgaagaagctctccttctattatctgataatggcaaagggaggcatt
gtccgaactgggactcatggactgcttgtgaagcaggaagacatgaagggccatttttccatctcaatccctgtgaagtcagacattgctc
ctgtcgctcggttgctcatctatgctgttttaccttaccggggacgtgattgggggattctgcaaaatatgatgttgaaaattgtctggccaacaa
ggtgaatttgagcttcagcccatcacaaagtctcccagcctcacacgcccacctgcgagtcacagcggctcctcagtccgtctgcgccct
ccgtgctgtggaccaaagcgtgctgctcatgaagcctgatgctgagctctcggcgtcctcggtttacaacctgctaccagaaaaggacct
cactggcttccctgggcctttgaatgaccaggacgatgaagactgcatcaatcgtcataatgtctatattaatggaatcacatatactccag
tatcaagtacaaatgaaaaggatatgtacagcttcctagaggacatgggcttaaaggcattcaccaactcaaagattcgtaaacccaaa
atgtgtccacagcttcaacagtatgaaatgcatggacctgaaggtctacgtgtaggtttttatgagtcagatgtaatgggaagaggccatg
cacgcctggtgcatgttgaagagcctcacacggagaccgtacgaaagtacttccctgagacatggatctgggatttggtggtggtaaact
cagcaggtgtggctgaggtaggagtaacagtccctgacaccatcaccgagtggaaggcaggggccttctgcctgtctgaagatgctgg
acttggtatctcttccactgcctctctccgagccttccagcccttctttgtggagctcacaatgccttactctgtgattcgtggagaggccttcac
actcaaggccacggtcctaaactaccttcccaaatgcatccgggtcagtgtgcagctggaagcctctcccgccttcctagctgtcccagtg
gagaaggaacaagcgcctcactgcatctgtgcaaacgggcggcaaactgtgtcctgggcagtaaccccaaagtcattaggaaatgtg
aatttcactgtgagcgcagaggcactagagtctcaagagctgtgtgggactgaggtgccttcagttcctgaacacggaaggaaagaca
cagtcatcaagcctctgttggttgaacctgaaggactagagaaggaaacaacattcaactccctacttttgtccatcaggtggtgaggtttct
gaagaattatccctgaaactgccaccaaatgtggtagaagaatctgcccgagcttctgtctcagttttgggagacatatattaggctctgccat
gcaaaacacacaaaatcttctccagatgccctatggctgtggagagcagaatatggtcctctttgctcctaacatctatgtactggattatct
aaatgaaacacagcagcttactccagagatcaagtccaaggccattggctatctcaacactggttaccagagacagttgaactacaaa
cactatgatggctcctacagcacctttggggagcgatatggcaggaaccagggcaacacctggctcacagcctttgttctgaagactttg
cccaagctcgagcctacatcttcatcgatgaagcacacattacccaagccctcatatggctctcccagaggcagaaggacaatggctgt
ttcaggagctctgggtcactgctcaacaatgccataaagggaggagtagaagatgaagtgaccctctccgcctatatcaccatcgcccatt
ctggagattcctctcacagtcactcaccctgttgtccgcaatgcccctgttttgcctggagtcagcctggaagacagcacaagaaggggac
catggcagccatgtatataccaaagcactgctggcctatgcttttgccctggcaggtaaccaggacaagaggaaggaagtactcaagt
cacttaatgaggaagctgtgaagaaagacaactctgtccattgggagcgccctcagaaacccaaggcaccagtggggcattttacga
accccaggctccctctgctgaggtggagatgacatcctatgtgctcctcgcttatctcacggcccagccagcccaacctcggaggacct
gacctctgcaaccaacatcgtgaagtggatcacgaagcagcagaatgcccagggcggttctcctccacccaggacacagtggtggc
tctccatgctctgtccaaatatggagcagccacatttaccaggactggaaggctgcacaggtgactatccagtcttcagggacatttcc
agcaaattccaagtggacaacaacaaccgcctgttactgcagcaggtcattgccagagctgcctggggaatacagcatgaaagtg
acaggagaaggatgtgtctacctccagacatccttgaaatacaatattctcccagaaaaggaagagttccccttgctttaggagtgcag
actctgcctcaaacttgtgatgaacccaaagcccacaccagcttccaaatctccctaagtgtcagttacacagggagccgctctgcctcc
aacatggcgatcgttgatgtgaagatggtctctggcttcattcccctgaagccaacagtgaaaatgcttgaaagatctaaccatgtgagcc
ggacagaagtcagcagcaaccatgtcttgatttaccttgataaggtgtcaaatcagacactgagcttgttcttcacggttctgcaagatgtc
ccagtaagagatctgaaaccagccatagtgaaagtctatgattactacgagacggatgagtttgcaattgctgagtacaatgctccttgca
gcaaagatcttggaaatgcttgaagaccacaaggctgaaaagtgctttgctggagtcctgttctcagagctccacagaagacacgtgtttt
tgtatctttaaagacttgatgaataaacactttttctggtcaatgtcaaaaaaaaaaaaaaaaaaaaaaaa
(SEQ ID NO: 6).

Figure 19

The FGG (Isoform gamma-A) human protein sequences is:
MSWSLHPRNLILYFYALLFLSSTCVAYVATRDNCCILDERFGSYCPTTCGIADFLSTYQT
KVDKDLQSLEDILHQVENKTSEVKQLIKAIQLTYNPDESSKPNMIDAATLKSRKMLEEIM
KYEASILTHDSSIRYLQEIYNSNNQKIVNLKEKVAQLEAQCQEPCKDTVQIHDITGKDCQ
DIANKGAKQSGLYFIKPLKANQQFLVYCEIDGSGNGWTVFQKRLDGSVDFKKNWIQYK
EGFGHLSPTGTTEFWLGNEKIHLISTQSAIPYALRVELEDWNGRTSTADYAMFKVGPEA
DKYRLTYAYFAGGDAGDAFDGFDFGDDPSDKFFTSHNGMQFSTWDNDNDKFEGNCA
EQDGSGWWMNKCHAGHLNGVYYQGGTYSKASTPNGYDNGIIWATWKTRWYSMKKT
TMKIIPFNRLTI
GEGQQHHLGGAKQAGDV (SEQ ID NO: 7)

The FGG (Isoform gamma-B) human protein sequences is:
MSWSLHPRNLILYFYALLFLSSTCVAYVATRDNCCILDERFGSYCPTTCGIADFLSTYQT
KVDKDLQSLEDILHQVENKTSEVKQLIKAIQLTYNPDESSKPNMIDAATLKSRKMLEEIM
KYEASILTHDSSIRYLQEIYNSNNQKIVNLKEKVAQLEAQCQEPCKDTVQIHDITGKDCQ
DIANKGAKQSGLYFIKPLKANQQFLVYCEIDGSGNGWTVFQKRLDGSVDFKKNWIQYK
EGFGHLSPTGTTEFWLGNEKIHLISTQSAIPYALRVELEDWNGRTSTADYAMFKVGPEA
DKYRLTYAYFAGGDAGDAFDGFDFGDDPSDKFFTSHNGMQFSTWDNDNDKFEGNCA
EQDGSGWWMNKCHAGHLNGVYYQGGTYSKASTPNGYDNGIIWATWKTRWYSMKKT
TMKIIPFNRLTIGEGQQHHLGGAKQVRPEHPAETEYDSLYPEDDL (SEQ ID NO: 8)

Figure 20
The FGG (Isoform gamma-A) human nucleic acid sequences is:
CTTCTGGTAAGGAGGCCCCGTGATCAGCTCCAGCCATTTGCAGTCCTGGCTATCCC
AGGAGCTTACATAAAGGGACAATTGGAGCCTGAGAGGTGACAGTGCTGACACTACA
AGGCTCGGAGCTCCGGGCACTCAGACATCATGAGTTGGTCCTTGCACCCCCGGAA
TTTAATTCTCTACTTCTATGCTCTTTTATTTCTCTCTTCAACATGTGTAGCATATGTTG
CTACCAGAGACAACTGCTGCATCTTAGATGAAAGATTCGGTAGTTATTGTCCAACTA
CCTGTGGCATTGCAGATTTCCTGTCTACTTATCAAACCAAAGTAGACAAGGATCTAC
AGTCTTTGGAAGACATCTTACATCAAGTTGAAAACAAAACATCAGAAGTCAAACAGC
TGATAAAAGCAATCCAACTCACTTATAATCCTGATGAATCATCAAAACCAAATATGAT
AGACGCTGCTACTTTGAAGTCCAGGAAAATGTTAGAAGAAATTATGAAATATGAAGC
ATCGATTTTAACACATGACTCAAGTATTCGATATTTGCAGGAAATATATAATTCAAAT
AATCAAAAGATTGTTAACCTGAAAGAGAAGGTAGCCCAGCTTGAAGCACAGTGCCA
GGAACCTTGCAAAGACACGGTGCAAATCCATGATATCACTGGGAAAGATTGTCAAG
ACATTGCCAATAAGGGAGCTAAACAGAGCGGGCTTTACTTTATTAAACCTCTGAAAG
CTAACCAGCAATTCTTAGTCTACTGTGAAATCGATGGGTCTGGAAATGGATGGACT
GTGTTTCAGAAGAGACTTGATGGCAGTGTAGATTTCAAGAAAAACTGGATTCAATAT
AAAGAAGGATTTGGACATCTGTCTCCTACTGGCACAACAGAATTTTGGCTGGGAAA
TGAGAAGATTCATTTGATAAGCACACAGTCTGCCATCCCATATGCATTAAGAGTGGA
ACTGGAAGACTGGAATGGCAGAACCAGTACTGCAGACTATGCCATGTTCAAGGTGG
GACCTGAAGCTGACAAGTACCGCCTAACATATGCCTACTTCGCTGGTGGGGATGCT
GGAGATGCCTTTGATGGCTTTGATTTTGGCGATGATCCTAGTGACAAGTTTTTCACA
TCCCATAATGGCATGCAGTTCAGTACCTGGGACAATGACAATGATAAGTTTGAAGG
CAACTGTGCTGAACAGGATGGATCTGGTTGGTGGATGAACAAGTGTCACGCTGGC
CATCTCAATGGAGTTTATTACCAAGGTGGCACTTACTCAAAAGCATCTACTCCTAAT
GGTTATGATAATGGCATTATTTGGGCCACTTGGAAAACCCGGTGGTATTCCATGAA
GAAAACCACTATGAAGATAATCCCATTCAACAGACTCACAATTGGAGAAGGACAGC
AACACCACCTGGGGGGAGCCAAACAGGCTGGAGACGTTTAAAAGACCGTTTCAAA
AGAGATTTACTTTTTTAAAGGACTTTATCTGAACAGAGAGATATAATATTTTTCCTATT
GGACAATGGACTTGCAAAGCTTCACTTCATTTTAAGAGCAAAAGACCCCATGTTGAA
AACTCCATAACAGTTTTATGCTGATGATAATTTATCTACATGCATTTCAATAAACCTTT
TGTTTCCTAAGACTAGAAAAA (SEQ ID NO: 9)

Figure 21
The FGG (Isoform gamma-B) human nucleic acid sequences is:
CTTCTGGTAAGGAGGCCCCGTGATCAGCTCCAGCCATTTGCAGTCCTGGCTATCCC
AGGAGCTTACATAAAGGGACAATTGGAGCCTGAGAGGTGACAGTGCTGACACTACA
AGGCTCGGAGCTCCGGGCACTCAGACATCATGAGTTGGTCCTTGCACCCCCGGAA
TTTAATTCTCTACTTCTATGCTCTTTTATTTCTCTCTTCAACATGTGTAGCATATGTTG
CTACCAGAGACAACTGCTGCATCTTAGATGAAAGATTCGGTAGTTATTGTCCAACTA
CCTGTGGCATTGCAGATTTCCTGTCTACTTATCAAACCAAAGTAGACAAGGATCTAC
AGTCTTTGGAAGACATCTTACATCAAGTTGAAAACAAAACATCAGAAGTCAAACAGC
TGATAAAAGCAATCCAACTCACTTATAATCCTGATGAATCATCAAAACCAAATATGAT
AGACGCTGCTACTTTGAAGTCCAGGAAAATGTTAGAAGAAATTATGAAATATGAAGC
ATCGATTTTAACACATGACTCAAGTATTCGATATTTGCAGGAAATATATAATTCAAAT
AATCAAAAGATTGTTAACCTGAAAGAGAAGGTAGCCCAGCTTGAAGCACAGTGCCA
GGAACCTTGCAAAGACACGGTGCAAATCCATGATATCACTGGGAAAGATTGTCAAG
ACATTGCCAATAAGGGAGCTAAACAGAGCGGGCTTTACTTTATTAAACCTCTGAAAG
CTAACCAGCAATTCTTAGTCTACTGTGAAATCGATGGGTCTGGAAATGGATGGACT
GTGTTTCAGAAGAGACTTGATGGCAGTGTAGATTTCAAGAAAAACTGGATTCAATAT
AAAGAAGGATTTGGACATCTGTCTCCTACTGGCACAACAGAATTTTGGCTGGGAAA
TGAGAAGATTCATTTGATAAGCACACAGTCTGCCATCCCATATGCATTAAGAGTGGA
ACTGGAAGACTGGAATGGCAGAACCAGTACTGCAGACTATGCCATGTTCAAGGTGG
GACCTGAAGCTGACAAGTACCGCCTAACATATGCCTACTTCGCTGGTGGGGATGCT
GGAGATGCCTTTGATGGCTTTGATTTTGGCGATGATCCTAGTGACAAGTTTTTCACA
TCCCATAATGGCATGCAGTTCAGTACCTGGGACAATGACAATGATAAGTTTGAAGG
CAACTGTGCTGAACAGGATGGATCTGGTTGGTGGATGAACAAGTGTCACGCTGGC
CATCTCAATGGAGTTTATTACCAAGGTGGCACTTACTCAAAAGCATCTACTCCTAAT
GGTTATGATAATGGCATTATTTGGGCCACTTGGAAAACCCGGTGGTATTCCATGAA
GAAAACCACTATGAAGATAATCCCATTCAACAGACTCACAATTGGAGAAGGACAGC
AACACCACCTGGGGGGAGCCAAACAGGTCAGACCAGAGCACCCTGCGGAAACAGA
ATATGACTCACTTTACCCTGAGGATGATTTGTAGAAAATTAACTGCTAACTTCTATTG
ACCCACAAAGTTTCAGAAATTCTCTGAAAGTTTCTTCCTTTTTTCTCTTACTATATTTA
TTGATTTCAAGTCTTCTATTAAGGACATTTAGCCTTCAATGGAAATTAAAACTCATTT
AGGACTGTATTTCCAAATTACTGATATCAGAGTTATTTAAAAATTGTTTATTTGAGGA
GATAACATTTCAACTTTGTTCCTAAATATATAATAATAAAATGATTGACTTTATTTGCA
AA (SEQ ID NO: 10)

SEQUENCE LISTING

<160> NUMBER OF SEQ ID NOS: 10

<210> SEQ ID NO 1
<211> LENGTH: 485
<212> TYPE: PRT
<213> ORGANISM: Homo sapiens

<400> SEQUENCE: 1

```
Met Arg Lys Arg Ala Pro Gln Ser Glu Met Ala Pro Ala Gly Val Ser
1               5                   10                  15

Leu Arg Ala Thr Ile Leu Cys Leu Leu Ala Trp Ala Gly Leu Ala Ala
            20                  25                  30

Gly Asp Arg Val Tyr Ile His Pro Phe His Leu Val Ile His Asn Glu
        35                  40                  45

Ser Thr Cys Glu Gln Leu Ala Lys Ala Asn Ala Gly Lys Pro Lys Asp
    50                  55                  60

Pro Thr Phe Ile Pro Ala Pro Ile Gln Ala Lys Thr Ser Pro Val Asp
65                  70                  75                  80

Glu Lys Ala Leu Gln Asp Gln Leu Val Leu Val Ala Ala Lys Leu Asp
                85                  90                  95

Thr Glu Asp Lys Leu Arg Ala Ala Met Val Gly Met Leu Ala Asn Phe
            100                 105                 110

Leu Gly Phe Arg Ile Tyr Gly Met His Ser Glu Leu Trp Gly Val Val
        115                 120                 125

His Gly Ala Thr Val Leu Ser Pro Thr Ala Val Phe Gly Thr Leu Ala
    130                 135                 140

Ser Leu Tyr Leu Gly Ala Leu Asp His Thr Ala Asp Arg Leu Gln Ala
145                 150                 155                 160

Ile Leu Gly Val Pro Trp Lys Asp Lys Asn Cys Thr Ser Arg Leu Asp
                165                 170                 175

Ala His Lys Val Leu Ser Ala Leu Gln Ala Val Gln Gly Leu Leu Val
            180                 185                 190

Ala Gln Gly Arg Ala Asp Ser Gln Ala Gln Leu Leu Leu Ser Thr Val
        195                 200                 205

Val Gly Val Phe Thr Ala Pro Gly Leu His Leu Lys Gln Pro Phe Val
    210                 215                 220

Gln Gly Leu Ala Leu Tyr Thr Pro Val Val Leu Pro Arg Ser Leu Asp
225                 230                 235                 240

Phe Thr Glu Leu Asp Val Ala Ala Glu Lys Ile Asp Arg Phe Met Gln
                245                 250                 255

Ala Val Thr Gly Trp Lys Thr Gly Cys Ser Leu Met Gly Ala Ser Val
            260                 265                 270

Asp Ser Thr Leu Ala Phe Asn Thr Tyr Val His Phe Gln Gly Lys Met
        275                 280                 285

Lys Gly Phe Ser Leu Leu Ala Glu Pro Gln Glu Phe Trp Val Asp Asn
    290                 295                 300

Ser Thr Ser Val Ser Val Pro Met Leu Ser Gly Met Gly Thr Phe Gln
305                 310                 315                 320
```

His Trp Ser Asp Ile Gln Asp Asn Phe Ser Val Thr Gln Val Pro Phe
            325                 330                 335

Thr Glu Ser Ala Cys Leu Leu Leu Ile Gln Pro His Tyr Ala Ser Asp
            340                 345                 350

Leu Asp Lys Val Glu Gly Leu Thr Phe Gln Gln Asn Ser Leu Asn Trp
            355                 360                 365

Met Lys Lys Leu Ser Pro Arg Thr Ile His Leu Thr Met Pro Gln Leu
            370                 375                 380

Val Leu Gln Gly Ser Tyr Asp Leu Gln Asp Leu Ala Gln Ala Glu
385                 390                 395                 400

Leu Pro Ala Ile Leu His Thr Glu Leu Asn Leu Gln Lys Leu Ser Asn
            405                 410                 415

Asp Arg Ile Arg Val Gly Glu Val Leu Asn Ser Ile Phe Phe Glu Leu
            420                 425                 430

Glu Ala Asp Glu Arg Glu Pro Thr Glu Ser Thr Gln Gln Leu Asn Lys
            435                 440                 445

Pro Glu Val Leu Glu Val Thr Leu Asn Arg Pro Phe Leu Phe Ala Val
            450                 455                 460

Tyr Asp Gln Ser Ala Thr Ala Leu His Phe Leu Gly Arg Val Ala Asn
465                 470                 475                 480

Pro Leu Ser Thr Ala
            485

<210> SEQ ID NO 2
<211> LENGTH: 462
<212> TYPE: PRT
<213> ORGANISM: Homo sapiens

<400> SEQUENCE: 2

Met Ala Arg Val Leu Gly Ala Pro Val Ala Leu Gly Leu Trp Ser Leu
1               5                   10                  15

Cys Trp Ser Leu Ala Ile Ala Thr Pro Leu Pro Pro Thr Ser Ala His
            20                  25                  30

Gly Asn Val Ala Glu Gly Glu Thr Lys Pro Asp Pro Asp Val Thr Glu
            35                  40                  45

Arg Cys Ser Asp Gly Trp Ser Phe Asp Ala Thr Thr Leu Asp Asp Asn
            50                  55                  60

Gly Thr Met Leu Phe Phe Lys Gly Glu Phe Val Trp Lys Ser His Lys
65                  70                  75                  80

Trp Asp Arg Glu Leu Ile Ser Glu Arg Trp Lys Asn Phe Pro Ser Pro
            85                  90                  95

Val Asp Ala Ala Phe Arg Gln Gly His Asn Ser Val Phe Leu Ile Lys
            100                 105                 110

Gly Asp Lys Val Trp Val Tyr Pro Pro Glu Lys Lys Glu Lys Gly Tyr
            115                 120                 125

Pro Lys Leu Leu Gln Asp Glu Phe Pro Gly Ile Pro Ser Pro Leu Asp
            130                 135                 140

Ala Ala Val Glu Cys His Arg Gly Glu Cys Gln Ala Glu Gly Val Leu
145                 150                 155                 160

Phe Phe Gln Gly Asp Arg Glu Trp Phe Trp Asp Leu Ala Thr Gly Thr
            165                 170                 175

Met Lys Glu Arg Ser Trp Pro Ala Val Gly Asn Cys Ser Ser Ala Leu
            180                 185                 190

Arg Trp Leu Gly Arg Tyr Tyr Cys Phe Gln Gly Asn Gln Phe Leu Arg
            195                 200                 205

Phe Asp Pro Val Arg Gly Glu Val Pro Pro Arg Tyr Pro Arg Asp Val
    210                 215                 220

Arg Asp Tyr Phe Met Pro Cys Pro Gly Arg Gly His Gly His Arg Asn
225                 230                 235                 240

Gly Thr Gly His Gly Asn Ser Thr His His Gly Pro Glu Tyr Met Arg
                245                 250                 255

Cys Ser Pro His Leu Val Leu Ser Ala Leu Thr Ser Asp Asn His Gly
            260                 265                 270

Ala Thr Tyr Ala Phe Ser Gly Thr His Tyr Trp Arg Leu Asp Thr Ser
        275                 280                 285

Arg Asp Gly Trp His Ser Trp Pro Ile Ala His Gln Trp Pro Gln Gly
290                 295                 300

Pro Ser Ala Val Asp Ala Ala Phe Ser Trp Glu Glu Lys Leu Tyr Leu
305                 310                 315                 320

Val Gln Gly Thr Gln Val Tyr Val Phe Leu Thr Lys Gly Gly Tyr Thr
                325                 330                 335

Leu Val Ser Gly Tyr Pro Lys Arg Leu Glu Lys Glu Val Gly Thr Pro
            340                 345                 350

His Gly Ile Ile Leu Asp Ser Val Asp Ala Ala Phe Ile Cys Pro Gly
        355                 360                 365

Ser Ser Arg Leu His Ile Met Ala Gly Arg Arg Leu Trp Trp Leu Asp
370                 375                 380

Leu Lys Ser Gly Ala Gln Ala Thr Trp Thr Glu Leu Pro Trp Pro His
385                 390                 395                 400

Glu Lys Val Asp Gly Ala Leu Cys Met Glu Lys Ser Leu Gly Pro Asn
                405                 410                 415

Ser Cys Ser Ala Asn Gly Pro Gly Leu Tyr Leu Ile His Gly Pro Asn
            420                 425                 430

Leu Tyr Cys Tyr Ser Asp Val Glu Lys Leu Asn Ala Ala Lys Ala Leu
        435                 440                 445

Pro Gln Pro Gln Asn Val Thr Ser Leu Leu Gly Cys Thr His
450                 455                 460

<210> SEQ ID NO 3
<211> LENGTH: 1474
<212> TYPE: PRT
<213> ORGANISM: Homo sapiens

<400> SEQUENCE: 3

Met Gly Lys Asn Lys Leu Leu His Pro Ser Leu Val Leu Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu

-continued

```
            115                 120                 125
Val Phe Val Gln Thr Asp Lys Ser Ile Tyr Lys Pro Gly Gln Thr Val
        130                 135                 140
Lys Phe Arg Val Val Ser Met Asp Glu Asn Phe His Pro Leu Asn Glu
145                 150                 155                 160
Leu Ile Pro Leu Val Tyr Ile Gln Asp Pro Lys Gly Asn Arg Ile Ala
                165                 170                 175
Gln Trp Gln Ser Phe Gln Leu Glu Gly Gly Leu Lys Gln Phe Ser Phe
            180                 185                 190
Pro Leu Ser Ser Glu Pro Phe Gln Gly Ser Tyr Lys Val Val Val Gln
                195                 200                 205
Lys Lys Ser Gly Gly Arg Thr Glu His Pro Phe Thr Val Glu Glu Phe
210                 215                 220
Val Leu Pro Lys Phe Glu Val Gln Val Thr Val Pro Lys Ile Ile Thr
225                 230                 235                 240
Ile Leu Glu Glu Glu Met Asn Val Ser Val Cys Gly Leu Tyr Thr Tyr
                245                 250                 255
Gly Lys Pro Val Pro Gly His Val Thr Val Ser Ile Cys Arg Lys Tyr
            260                 265                 270
Ser Asp Ala Ser Asp Cys His Gly Glu Asp Ser Gln Ala Phe Cys Glu
                275                 280                 285
Lys Phe Ser Gly Gln Leu Asn Ser His Gly Cys Phe Tyr Gln Gln Val
        290                 295                 300
Lys Thr Lys Val Phe Gln Leu Lys Arg Lys Glu Tyr Glu Met Lys Leu
305                 310                 315                 320
His Thr Glu Ala Gln Ile Gln Glu Gly Thr Val Val Glu Leu Thr
                325                 330                 335
Gly Arg Gln Ser Ser Glu Ile Thr Arg Thr Ile Thr Lys Leu Ser Phe
            340                 345                 350
Val Lys Val Asp Ser His Phe Arg Gln Gly Ile Pro Phe Phe Gly Gln
                355                 360                 365
Val Arg Leu Val Asp Gly Lys Gly Val Pro Ile Pro Asn Lys Val Ile
        370                 375                 380
Phe Ile Arg Gly Asn Glu Ala Asn Tyr Tyr Ser Asn Ala Thr Thr Asp
385                 390                 395                 400
Glu His Gly Leu Val Gln Phe Ser Ile Asn Thr Thr Asn Val Met Gly
                405                 410                 415
Thr Ser Leu Thr Val Arg Val Asn Tyr Lys Asp Arg Ser Pro Cys Tyr
            420                 425                 430
Gly Tyr Gln Trp Val Ser Glu Glu His Glu Glu Ala His His Thr Ala
                435                 440                 445
Tyr Leu Val Phe Ser Pro Ser Lys Ser Phe Val His Leu Glu Pro Met
        450                 455                 460
Ser His Glu Leu Pro Cys Gly His Thr Gln Thr Val Gln Ala His Tyr
465                 470                 475                 480
Ile Leu Asn Gly Gly Thr Leu Leu Gly Leu Lys Lys Leu Ser Phe Tyr
                485                 490                 495
Tyr Leu Ile Met Ala Lys Gly Gly Ile Val Arg Thr Gly Thr His Gly
            500                 505                 510
Leu Leu Val Lys Gln Glu Asp Met Lys Gly His Phe Ser Ile Ser Ile
                515                 520                 525
Pro Val Lys Ser Asp Ile Ala Pro Val Ala Arg Leu Leu Ile Tyr Ala
        530                 535                 540
```

```
Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
            565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
            595                 600                 605

Pro Asp Ala Glu Leu Ser Ala Ser Ser Val Tyr Asn Leu Leu Pro Glu
        610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
            675                 680                 685

Cys Pro Gln Leu Gln Gln Tyr Glu Met His Gly Pro Glu Gly Leu Arg
        690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
        770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
            915                 920                 925

Glu Glu Leu Ser Leu Lys Leu Pro Pro Asn Val Val Glu Glu Ser Ala
        930                 935                 940

Arg Ala Ser Val Ser Val Leu Gly Asp Ile Leu Gly Ser Ala Met Gln
945                 950                 955                 960
```

```
Asn Thr Gln Asn Leu Leu Gln Met Pro Tyr Gly Cys Gly Glu Gln Asn
            965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
            995                 1000                1005

Asn Thr Gly Tyr Gln Arg Gln Leu Asn Tyr Lys His Tyr Asp Gly
        1010                1015                1020

Ser Tyr Ser Thr Phe Gly Glu Arg Tyr Gly Arg Asn Gln Gly Asn
        1025                1030                1035

Thr Trp Leu Thr Ala Phe Val Leu Lys Thr Phe Ala Gln Ala Arg
        1040                1045                1050

Ala Tyr Ile Phe Ile Asp Glu Ala His Ile Thr Gln Ala Leu Ile
        1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Gly Val Glu Asp Glu
        1085                1090                1095

Val Thr Leu Ser Ala Tyr Ile Thr Ile Ala Leu Leu Glu Ile Pro
        1100                1105                1110

Leu Thr Val Thr His Pro Val Val Arg Asn Ala Leu Phe Cys Leu
        1115                1120                1125

Glu Ser Ala Trp Lys Thr Ala Gln Glu Gly Asp His Gly Ser His
        1130                1135                1140

Val Tyr Thr Lys Ala Leu Leu Ala Tyr Ala Phe Ala Leu Ala Gly
        1145                1150                1155

Asn Gln Asp Lys Arg Lys Glu Val Leu Lys Ser Leu Asn Glu Glu
        1160                1165                1170

Ala Val Lys Lys Asp Asn Ser Val His Trp Glu Arg Pro Gln Lys
        1175                1180                1185

Pro Lys Ala Pro Val Gly His Phe Tyr Glu Pro Gln Ala Pro Ser
        1190                1195                1200

Ala Glu Val Glu Met Thr Ser Tyr Val Leu Leu Ala Tyr Leu Thr
        1205                1210                1215

Ala Gln Pro Ala Pro Thr Ser Glu Asp Leu Thr Ser Ala Thr Asn
        1220                1225                1230

Ile Val Lys Trp Ile Thr Lys Gln Gln Asn Ala Gln Gly Gly Phe
        1235                1240                1245

Ser Ser Thr Gln Asp Thr Val Val Ala Leu His Ala Leu Ser Lys
        1250                1255                1260

Tyr Gly Ala Ala Thr Phe Thr Arg Thr Gly Lys Ala Ala Gln Val
        1265                1270                1275

Thr Ile Gln Ser Ser Gly Thr Phe Ser Ser Lys Phe Gln Val Asp
        1280                1285                1290

Asn Asn Asn Arg Leu Leu Leu Gln Gln Val Ser Leu Pro Glu Leu
        1295                1300                1305

Pro Gly Glu Tyr Ser Met Lys Val Thr Gly Glu Gly Cys Val Tyr
        1310                1315                1320

Leu Gln Thr Ser Leu Lys Tyr Asn Ile Leu Pro Glu Lys Glu Glu
        1325                1330                1335

Phe Pro Phe Ala Leu Gly Val Gln Thr Leu Pro Gln Thr Cys Asp
        1340                1345                1350

Glu Pro Lys Ala His Thr Ser Phe Gln Ile Ser Leu Ser Val Ser
```

```
            1355               1360              1365
Tyr Thr Gly Ser Arg Ser Ala Ser Asn Met Ala Ile Val Asp Val
        1370              1375              1380

Lys Met Val Ser Gly Phe Ile Pro Leu Lys Pro Thr Val Lys Met
        1385              1390              1395

Leu Glu Arg Ser Asn His Val Ser Arg Thr Glu Val Ser Ser Asn
        1400              1405              1410

His Val Leu Ile Tyr Leu Asp Lys Val Ser Asn Gln Thr Leu Ser
        1415              1420              1425

Leu Phe Phe Thr Val Leu Gln Asp Val Pro Val Arg Asp Leu Lys
        1430              1435              1440

Pro Ala Ile Val Lys Val Tyr Asp Tyr Tyr Glu Thr Asp Glu Phe
        1445              1450              1455

Ala Ile Ala Glu Tyr Asn Ala Pro Cys Ser Lys Asp Leu Gly Asn
        1460              1465              1470

Ala

<210> SEQ ID NO 4
<211> LENGTH: 2587
<212> TYPE: DNA
<213> ORGANISM: Homo sapiens

<400> SEQUENCE: 4
atcccatgag cgggcagcag ggtcagaagt ggcccccgtg ttgcctaagc aagactctcc      60
cctgccctct gccctctgca cctccggcct gcatgtccct gtggcctctt gggggtacat     120
ctcccggggc tgggtcagaa ggcctgggtg gttggcctca ggctgtcaca cacctaggga    180
gatgctcccg tttctgggaa ccttggcccc gactcctgca aacttcggta atgtgtaac     240 tcgaccctgc accggctcac tctgttcagc agtgaaactc tgcatcgatc actaagactt    300
cctggaagag gtcccagcgt gagtgtcgct tctggcatct gtccttctgg ccagcctgtg    360
gtctggccaa gtgatgtaac cctcctctcc agcctgtgca caggcagcct gggaacagct    420
ccatccccac ccctcagcta taaatagggc atcgtgaccc ggccggggga agaagctgcc    480
gttgttctgg gtactacagc agaagggtat gcggaagcga gcaccccagt ctgagatggc    540
tcctgccggt gtgagcctga gggccaccat cctctgcctc ctggcctggg ctggcctggc    600
tgcaggtgac cgggtgtaca tacaccccct tccacctcgtc atccacaatg agagtacctg    660
tgagcagctg gcaaaggcca atgccgggaa gcccaaagac cccaccttca tacctgctcc    720
aattcaggcc aagacatccc ctgtggatga aaaggcccta caggaccagc tggtgctagt    780
cgctgcaaaa cttgacaccg aagacaagtt gagggccgca atggtcggga tgctggccaa    840
cttcttgggc ttccgtatat atggcatgca cagtgagcta tggggcgtgg tccatggggc    900
caccgtcctc tccccaacgg ctgtctttgg caccctggcc tctctctatc tgggagcctt    960
ggaccacaca gctgacaggc tacaggcaat cctgggtgtt ccttggaagg acaagaactg    1020
cacctcccgg ctggatgcgc acaaggtcct gtctgccctg caggctgtac agggcctgct    1080
agtgggccca ggcagggctg atagccaggc ccagctgctg ctgtccacgg tggtgggcgt    1140
gttcacagcc ccaggcctgc acctgaagca gccgtttgtg cagggcctgg ctctctatac    1200
ccctgtggtc ctcccacgct ctctggactt cacagaactg gatgttgctg ctgagaagat    1260
tgacaggttc atgcaggctg tgacaggatg gaagactggc tgctccctga tgggagccag    1320 tgtgacagc accctggctt tcaacaccta cgtccacttc caagggaaga tgaagggctt    1380
```

-continued

| | |
|---|---|
| ctccctgctg gccgagcccc aggagttctg ggtggacaac agcacctcag tgtctgttcc | 1440 |
| catgctctct ggcatgggca ccttccagca ctggagtgac atccaggaca acttctcggt | 1500 |
| gactcaagtg cccttcactg agagcgcctg cctgctgctg atccagcctc actatgcctc | 1560 |
| tgacctggac aaggtggagg gtctcacttt ccagcaaaac tccctcaact ggatgaagaa | 1620 |
| actatctccc cggaccatcc acctgaccat gccccaactg gtgctgcaag atcttatga | 1680 |
| cctgcaggac ctgctcgccc aggctgagct gcccgccatt ctgcacaccg agctgaacct | 1740 |
| gcaaaaattg agcaatgacc gcatcagggt gggggaggtg ctgaacagca ttttttttga | 1800 |
| gcttgaagcg gatgagagag agcccacaga gtctacccaa cagcttaaca agcctgaggt | 1860 |
| cttggaggtg accctgaacc gcccattcct gtttgctgtg tatgatcaaa gcgccactgc | 1920 |
| cctgcacttc ctgggccgcg tggccaaccc gctgagcaca gcatgaggcc agggccccag | 1980 |
| aacacagtgc ctggcaaggc ctctgcccct ggcctttgag gcaaaggcca gcagcagata | 2040 |
| acaaccccgg acaaatcagc gatgtgtcac ccccagtctc ccacctttc ttctaatgag | 2100 |
| tcgactttga gctggaaagc agccgttct ccttggtcta agtgtgctgc atggagtgag | 2160 |
| cagtagaagc ctgcagcggc acaaatgcac ctcccagttt gctgggttta ttttagagaa | 2220 |
| tgggggtggg gaggcaagaa ccagtgttta gcgcgggact actgttccaa aagaattcc | 2280 |
| aaccgaccag cttgtttgtg aaacaaaaaa gtgttccctt ttcaagttga gaacaaaaat | 2340 |
| tgggttttaa aattaaagta tacatttttg cattgccttc ggtttgtatt tagtgtcttg | 2400 |
| aatgtaagaa catgacctcc gtgtagtgtc tgtaatacct tagttttttc cacagatgct | 2460 |
| tgtgattttt gaacaatacg tgaaagatgc aagcacctga atttctgttt gaatgcggaa | 2520 |
| ccatagctgg ttatttctcc cttgtgttag taataaacgt cttgccacaa taagcctcca | 2580 |
| aaaaaaa | 2587 |

<210> SEQ ID NO 5
<211> LENGTH: 1635
<212> TYPE: DNA
<213> ORGANISM: Homo sapiens

<400> SEQUENCE: 5

| | |
|---|---|
| aactctatat agggagttca actggtcacc cagagctgtc ctgtggcctc tgcagctcag | 60 |
| catggctagg gtactgggag cacccgttgc actggggttg tggagcctat gctggtctct | 120 |
| ggccattgcc acccctcttc ctccgactag tgcccatggg aatgttgctg aaggcgagac | 180 |
| caagccagac ccagacgtga ctgaacgctg ctcagatggc tggagctttg atgctaccac | 240 |
| cctggatgac aatggaacca tgctgttttt taaagggag tttgtgtgga agagtcacaa | 300 |
| atgggaccgg gagttaatct cagagagatg aagaatttc cccagccctg tggatgctgc | 360 |
| attccgtcaa ggtcacaaca gtgtcttttct gatcaagggg acaaagtct gggtataccc | 420 |
| tcctgaaaag aaggagaaag gatacccaaa gttgctccaa gatgaatttc ctggaatccc | 480 |
| atccccactg gatgcagctg tggaatgtca ccgtggagaa tgtcaagctg aaggcgtcct | 540 |
| cttcttccaa ggtgaccgcg agtggttctg ggacttggct acgggaacca tgaaggagcg | 600 |
| ttcctggcca gctgttggga actgctcctc tgccctgaga tggctgggcc gctactactg | 660 |
| cttccagggt aaccaattcc tgcgcttcga ccctgtcagg ggagaggtgc ctcccaggta | 720 |
| cccgcgggat gtccgagact acttcatgcc ctgccctggc agaggccatg gacacaggaa | 780 |
| tgggactggc catgggaaca gtaccccacc tggccctgag tatatgcgct gtagcccaca | 840 |
| tctagtcttg tctgcactga cgtctgacaa ccatggtgcc acctatgcct tcagtgggac | 900 |

-continued

```
ccactactgg cgtctggaca ccagccggga tggctggcat agctggccca ttgctcatca      960
gtggccccag ggtccttcag cagtggatgc tgccttttcc tgggaagaaa aactctatct     1020
ggtccagggc acccaggtat atgtcttcct gacaaaggga ggctataccc tagtaagcgg     1080
ttatccgaag cggctggaga aggaagtcgg gaccccctcat gggattatcc tggactctgt    1140
ggatgcggcc tttatctgcc ctgggtcttc tcggctccat atcatggcag acggcggct     1200 gtggtggctg gacctgaagt caggagccca agccacgtgg acagagcttc cttgcccca     1260 tgagaaggta gacggagcct tgtgtatgga aaagtccctt ggccctaact catgttccgc    1320
caatggtccc ggcttgtacc tcatccatgg tcccaatttg tactgctaca gtgatgtgga    1380
gaaactgaat gcagccaagg cccttccgca accccagaat gtgaccagtc tcctgggctg    1440
cactcactga ggggccttct gacatgagtc tggcctggcc ccacctccta gttcctcata    1500
ataaagacag attgcttctt cgcttctcac tgagggcct tctgacatga gtctggcctg    1560
gccccacctc cccagtttct cataataaag acagattgct tcttcacttg aatcaaggga    1620
cctaaaaaaa aaaaa                                                     1635

<210> SEQ ID NO 6
<211> LENGTH: 4678
<212> TYPE: DNA
<213> ORGANISM: Homo sapiens

<400> SEQUENCE: 6
gcacacagag cagcataaag cccagttgct ttgggaagtg tttgggacca gatggattgt       60
agggagtagg gtacaataca gtctgttctc ctccagctcc ttctttctgc aacatgggga      120
agaacaaact ccttcatcca agtctggttc ttctcctctt ggtcctcctg cccacagacg      180
cctcagtctc tggaaaaccg cagtatatgg ttctggtccc ctccctgctc cacactgaga      240
ccactgagaa gggctgtgtc cttctgagct acctgaatga gacagtgact gtaagtgctt      300
ccttggagtc tgtcagggga aacaggagcc tcttcactga cctggaggcg agaatgacg      360 tactccactg tgtcgccttc gctgtcccaa agtcttcatc caatgaggag gtaatgttcc      420
tcactgtcca agtgaaagga ccaacccaag aatttaagaa gcggaccaca gtgatggtta      480
agaacgagga cagtctggtc tttgtccaga cagacaaatc aatctacaaa ccagggcaga      540
cagtgaaatt tcgtgttgtc tccatggatg aaaactttca ccccctgaat gagttgattc      600
cactagtata cattcaggat cccaaaggaa atcgcatcgc acaatggcag agtttccagt      660
tagagggtgg cctcaagcaa ttttcttttc ccctctcatc agagcccttc cagggctcct     720
acaaggtggt ggtacagaag aaatcaggtg gaaggacaga gcacccttc accgtggagg      780 aatttgttct tccaagtttt gaagtacaag taacagtgcc aaagataatc accatccttgg    840 aagaagagat gaatgtatca gtgtgtggcc tatacacata tgggaagcct gtccctggac     900
atgtgactgt gagcatttgc agaaagtata gtgacgcttc cgactgccac ggtgaagatt     960
cacaggcttt ctgtgagaaa ttcagtggac agctaaacag ccatggctgc ttctatcagc    1020
aagtaaaaac caaggtcttc cagctgaaga ggaaggagta tgaaatgaaa cttcacactg    1080
aggcccagat ccaagaagaa ggaacagtgg tggaattgac tggaaggcag tccagtgaaa    1140
tcacaagaac cataaccaaa ctctcatttg tgaaagtgga ctcacacttt cgacagggaa    1200
ttcccttctt tgggcaggtg cgcctagtag atgggaaagg cgtccctata ccaaataaag    1260
tcatattcat cagaggaaat gaagcaaact attactccaa tgctaccacg gatgagcatg    1320
```

```
gccttgtaca gttctctatc aacaccacca atgttatggg tacctctctt actgttaggg      1380
tcaattacaa ggatcgtagt ccctgttacg gctaccagtg ggtgtcagaa gaacacgaag      1440
aggcacatca cactgcttat cttgtgttct ccccaagcaa gagctttgtc caccttgagc      1500
ccatgtctca tgaactaccc tgtggccata ctcagacagt ccaggcacat tatattctga      1560
atggaggcac cctgctgggg ctgaagaagc tctccttcta ttatctgata atggcaaagg      1620
gaggcattgt ccgaactggg actcatggac tgcttgtgaa gcaggaagac atgaagggcc      1680 attttccat ctcaatccct gtgaagtcag acattgctcc tgtcgctcgg ttgctcatct       1740
atgctgtttt acctaccggg gacgtgattg gggattctgc aaaatatgat gttgaaaatt      1800
gtctggccaa caaggtggat tgagcttca gcccatcaca aagtctccca gcctcacacg       1860
cccacctgcg agtcacagcg gctcctcagt ccgtctgcgc cctccgtgct gtggaccaaa      1920
gcgtgctgct catgaagcct gatgctgagc tctcggcgtc ctcggtttac aacctgctac      1980
cagaaaagga cctcactggc ttccctgggc ctttgaatga ccaggacgat gaagactgca      2040
tcaatcgtca taatgtctat attaatgaaa tcacatatac tccagtatca agtacaaatg      2100
aaaaggatat gtacagcttc ctagaggaca tgggcttaaa ggcattcacc aactcaaaga      2160
ttcgtaaacc caaaatgtgt ccacagcttc aacagtatga aatgcatgga cctgaaggtc      2220
tacgtgtagg tttttatgag tcagatgtaa tgggaagagg ccatgcacgc ctggtgcatg      2280
ttgaagagcc tcacacggag accgtacgaa agtactccc tgagacatgg atctgggatt       2340
tggtggtggt aaactcagca ggtgtggctg aggtaggagt aacagtccct gacaccatca      2400
ccgagtggaa ggcaggggcc ttctgcctgt ctgaagatgc tggacttggt atctcttcca      2460
ctgcctctct ccgagccttc cagccctct ttgtggagct cacaatgcct tactctgtga       2520
ttcgtggaga ggccttcaca ctcaaggcca cggtcctaaa ctaccttccc aaatgcatcc      2580
gggtcagtgt gcagctggaa gcctctcccg ccttcctagc tgtcccagtg gagaaggaac      2640
aagcgcctca ctgcatctgt gcaaacgggc ggcaaactgt gtcctgggca gtaaccccaa      2700
agtcattagg aaatgtgaat ttcactgtga gcgcagaggc actagagtct caagagctgt      2760
gtgggactga ggtgccttca gttcctgaac acggaaggaa agacacagtc atcaagcctc      2820
tgttggttga acctgaagga ctagagaagg aaacaacatt caactcccta ctttgtccat      2880
caggtggtga ggtttctgaa gaattatccc tgaaactgcc accaaatgtg gtagaagaat      2940
ctgcccgagc ttctgtctca gttttgggag acatattagg ctctgccatg caaaacacac      3000
aaaatcttct ccagatgccc tatggctgtg gagagcagaa tatggtcctc tttgctccta      3060
acatctatgt actggattat ctaaatgaaa cacagcagct tactccagag atcaagtcca      3120
aggccattgg ctatctcaac actggttacc agagacagtt gaactacaaa cactatgatg      3180
gctcctacag caccttgggg agcgatatg gcaggaacca gggcaacacc tggctcacag       3240
cctttgttct gaagactttt gcccaagctc gagcctacat cttcatcgat gaagcacaca      3300
ttacccaagc cctcatatgg ctctcccaga ggcagaagga caatggctgt ttcaggagct      3360
ctgggtcact gctcaacaat gccataaagg gaggagtaga agatgaagtg accctctccg      3420
cctatatcac catcgccctt ctggagattc tctcacagt cactcaccct gttgtccgca      3480
atgccctgtt ttgcctggag tcagcctgga agacagcaca agaagggac catggcagcc      3540 atgtatatac caaagcactg ctggcctatg cttttgccct ggcaggtaac caggacaaga      3600
ggaaggaagt actcaagtca cttaatgagg aagctgtgaa gaaagacaac tctgtccatt      3660
gggagcgccc tcagaaaccc aaggcaccag tggggcattt ttacgaaccc caggctccct      3720
```

-continued

```
ctgctgaggt ggagatgaca tcctatgtgc tcctcgctta tctcacggcc cagccagccc    3780
caacctcgga ggacctgacc tctgcaacca acatcgtgaa gtggatcacg aagcagcaga    3840
atgcccaggg cggtttctcc tccacccagg acacagtggt ggctctccat gctctgtcca    3900
aatatggagc agccacattt accaggactg ggaaggctgc acaggtgact atccagtctt    3960
cagggacatt ttccagcaaa ttccaagtgg acaacaacaa ccgcctgtta ctgcagcagg    4020
tctcattgcc agagctgcct ggggaataca gcatgaaagt gacaggagaa ggatgtgtct    4080
acctccagac atccttgaaa tacaatattc tcccagaaaa ggaagagttc cctttgcttt    4140
taggagtgca gactctgcct caaacttgtg atgaacccaa agcccacacc agcttccaaa    4200
tctccctaag tgtcagttac acagggagcc gctctgcctc caacatggcg atcgttgatg    4260
tgaagatggt ctctggcttc attccctga agccaacagt gaaaatgctt gaaagatcta    4320
accatgtgag ccggacagaa gtcagcagca accatgtctt gatttacctt gataaggtgt    4380
caaatcagac actgagcttg ttcttcacgg ttctgcaaga tgtcccagta agagatctga    4440
aaccagccat agtgaaagtc tatgattact acgagacgga tgagtttgca attgctgagt    4500
acaatgctcc ttgcagcaaa gatcttggaa atgcttgaag accacaaggc tgaaaagtgc    4560
tttgctggag tcctgttctc agagctccac agaagacacg tgttttttgta tctttaaaga    4620
cttgatgaat aaaacacttt tctggtcaat gtcaaaaaaa aaaaaaaaaa aaaaaaa      4678
```

```
<210> SEQ ID NO 7
<211> LENGTH: 420
<212> TYPE: PRT
<213> ORGANISM: Homo sapiens

<400> SEQUENCE: 7
```

```
Met Ser Trp Ser Leu His Pro Arg Asn Leu Ile Leu Tyr Phe Tyr Ala
 1               5                  10                  15

Leu Leu Phe Leu Ser Ser Thr Cys Val Ala Tyr Val Ala Thr Arg Asp
            20                  25                  30

Asn Cys Cys Ile Leu Asp Glu Arg Phe Gly Ser Tyr Cys Pro Thr Thr
        35                  40                  45

Cys Gly Ile Ala Asp Phe Leu Ser Thr Tyr Gln Thr Lys Val Asp Lys
    50                  55                  60

Asp Leu Gln Ser Leu Glu Asp Ile Leu His Gln Val Glu Asn Lys Thr
65                  70                  75                  80

Ser Glu Val Lys Gln Leu Ile Lys Ala Ile Gln Leu Thr Tyr Asn Pro
                85                  90                  95

Asp Glu Ser Ser Lys Pro Asn Met Ile Asp Ala Ala Thr Leu Lys Ser
            100                 105                 110

Arg Lys Met Leu Glu Glu Ile Met Lys Tyr Glu Ala Ser Ile Leu Thr
        115                 120                 125

His Asp Ser Ser Ile Arg Tyr Leu Gln Glu Ile Tyr Asn Ser Asn Asn
    130                 135                 140

Gln Lys Ile Val Asn Leu Lys Glu Lys Val Ala Gln Leu Glu Ala Gln
145                 150                 155                 160

Cys Gln Glu Pro Cys Lys Asp Thr Val Gln Ile His Asp Ile Thr Gly
                165                 170                 175

Lys Asp Cys Gln Asp Ile Ala Asn Lys Gly Ala Lys Gln Ser Gly Leu
            180                 185                 190

Tyr Phe Ile Lys Pro Leu Lys Ala Asn Gln Gln Phe Leu Val Tyr Cys
        195                 200                 205
```

```
Glu Ile Asp Gly Ser Gly Asn Gly Trp Thr Val Phe Gln Lys Arg Leu
    210                 215                 220
Asp Gly Ser Val Asp Phe Lys Lys Asn Trp Ile Gln Tyr Lys Glu Gly
225                 230                 235                 240
Phe Gly His Leu Ser Pro Thr Gly Thr Thr Glu Phe Trp Leu Gly Asn
                245                 250                 255
Glu Lys Ile His Leu Ile Ser Thr Gln Ser Ala Ile Pro Tyr Ala Leu
            260                 265                 270
Arg Val Glu Leu Glu Asp Trp Asn Gly Arg Thr Ser Thr Ala Asp Tyr
        275                 280                 285
Ala Met Phe Lys Val Gly Pro Glu Ala Asp Lys Tyr Arg Leu Thr Tyr
    290                 295                 300
Ala Tyr Phe Ala Gly Gly Asp Ala Gly Asp Ala Phe Asp Gly Phe Asp
305                 310                 315                 320
Phe Gly Asp Asp Pro Ser Asp Lys Phe Phe Thr Ser His Asn Gly Met
                325                 330                 335
Gln Phe Ser Thr Trp Asp Asn Asp Asn Asp Lys Phe Glu Gly Asn Cys
            340                 345                 350
Ala Glu Gln Asp Gly Ser Gly Trp Trp Met Asn Lys Cys His Ala Gly
        355                 360                 365
His Leu Asn Gly Val Tyr Tyr Gln Gly Gly Thr Tyr Ser Lys Ala Ser
    370                 375                 380
Thr Pro Asn Gly Tyr Asp Asn Gly Ile Ile Trp Ala Thr Trp Lys Thr
385                 390                 395                 400
Arg Trp Tyr Ser Met Lys Lys Thr Thr Met Lys Ile Ile Pro Phe Asn
                405                 410                 415
Arg Leu Thr Ile
            420

<210> SEQ ID NO 8
<211> LENGTH: 453
<212> TYPE: PRT
<213> ORGANISM: Homo sapiens

<400> SEQUENCE: 8

Met Ser Trp Ser Leu His Pro Arg Asn Leu Ile Leu Tyr Phe Tyr Ala
1               5                   10                  15
Leu Leu Phe Leu Ser Ser Thr Cys Val Ala Tyr Val Ala Thr Arg Asp
                20                  25                  30
Asn Cys Cys Ile Leu Asp Glu Arg Phe Gly Ser Tyr Cys Pro Thr Thr
            35                  40                  45
Cys Gly Ile Ala Asp Phe Leu Ser Thr Tyr Gln Thr Lys Val Asp Lys
        50                  55                  60
Asp Leu Gln Ser Leu Glu Asp Ile Leu His Gln Val Glu Asn Lys Thr
65                  70                  75                  80
Ser Glu Val Lys Gln Leu Ile Lys Ala Ile Gln Leu Thr Tyr Asn Pro
                85                  90                  95
Asp Glu Ser Ser Lys Pro Asn Met Ile Asp Ala Ala Thr Leu Lys Ser
            100                 105                 110
Arg Lys Met Leu Glu Glu Ile Met Lys Tyr Glu Ala Ser Ile Leu Thr
        115                 120                 125
His Asp Ser Ser Ile Arg Tyr Leu Gln Glu Ile Tyr Asn Ser Asn Asn
    130                 135                 140
Gln Lys Ile Val Asn Leu Lys Glu Lys Val Ala Gln Leu Glu Ala Gln
```

```
                145                 150                 155                 160
Cys Gln Glu Pro Cys Lys Asp Thr Val Gln Ile His Asp Ile Thr Gly
                    165                 170                 175
Lys Asp Cys Gln Asp Ile Ala Asn Lys Gly Ala Lys Gln Ser Gly Leu
                180                 185                 190
Tyr Phe Ile Lys Pro Leu Lys Ala Asn Gln Gln Phe Leu Val Tyr Cys
            195                 200                 205
Glu Ile Asp Gly Ser Gly Asn Gly Trp Thr Val Phe Gln Lys Arg Leu
        210                 215                 220
Asp Gly Ser Val Asp Phe Lys Lys Asn Trp Ile Gln Tyr Lys Glu Gly
225                 230                 235                 240
Phe Gly His Leu Ser Pro Thr Gly Thr Thr Glu Phe Trp Leu Gly Asn
                245                 250                 255
Glu Lys Ile His Leu Ile Ser Thr Gln Ser Ala Ile Pro Tyr Ala Leu
            260                 265                 270
Arg Val Glu Leu Glu Asp Trp Asn Gly Arg Thr Ser Thr Ala Asp Tyr
        275                 280                 285
Ala Met Phe Lys Val Gly Pro Glu Ala Asp Lys Tyr Arg Leu Thr Tyr
290                 295                 300
Ala Tyr Phe Ala Gly Gly Asp Ala Gly Asp Ala Phe Asp Gly Phe Asp
305                 310                 315                 320
Phe Gly Asp Asp Pro Ser Asp Lys Phe Phe Thr Ser His Asn Gly Met
                325                 330                 335
Gln Phe Ser Thr Trp Asp Asn Asp Asn Asp Lys Phe Glu Gly Asn Cys
            340                 345                 350
Ala Glu Gln Asp Gly Ser Gly Trp Trp Met Asn Lys Cys His Ala Gly
        355                 360                 365
His Leu Asn Gly Val Tyr Tyr Gln Gly Gly Thr Tyr Ser Lys Ala Ser
    370                 375                 380
Thr Pro Asn Gly Tyr Asp Asn Gly Ile Ile Trp Ala Thr Trp Lys Thr
385                 390                 395                 400
Arg Trp Tyr Ser Met Lys Lys Thr Thr Met Lys Ile Ile Pro Phe Asn
                405                 410                 415
Arg Leu Thr Ile Gly Glu Gly Gln Gln His Leu Gly Gly Ala Lys
            420                 425                 430
Gln Val Arg Pro Glu His Pro Ala Glu Thr Glu Tyr Asp Ser Leu Tyr
        435                 440                 445
Pro Glu Asp Asp Leu
    450

<210> SEQ ID NO 9
<211> LENGTH: 1665
<212> TYPE: DNA
<213> ORGANISM: Homo sapiens

<400> SEQUENCE: 9
cttctggtaa ggaggccccg tgatcagctc cagccatttg cagtcctggc tatcccagga     60
gcttacataa agggacaatt ggagcctgag aggtgacagt gctgacacta caaggctcgg    120
agctccgggc actcagacat catgagttgg tccttgcacc ccggaatttt aattctctac    180
ttctatgctc ttttatttct ctcttcaaca tgtgtagcat atgttgctac cagagacaac    240
tgctgcatct tagatgaaag attcggtagt tattgtccaa ctacctgtgg cattgcagat    300
ttcctgtcta cttatcaaac caaagtagac aaggatctac agtctttgga agacatctta    360
```

-continued

| | |
|---|---|
| catcaagttg aaaacaaaac atcagaagtc aaacagctga taaaagcaat ccaactcact | 420 |
| tataatcctg atgaatcatc aaaaccaaat atgatagacg ctgctacttt gaagtccagg | 480 |
| aaaatgttag aagaaattat gaaatatgaa gcatcgattt taacacatga ctcaagtatt | 540 |
| cgatatttgc aggaaatata taattcaaat aatcaaaaga ttgttaacct gaaagagaag | 600 |
| gtagcccagc ttgaagcaca gtgccaggaa ccttgcaaag acacggtgca aatccatgat | 660 |
| atcactggga aagattgtca agacattgcc aataagggag ctaaacagag cgggctttac | 720 |
| tttattaaac ctctgaaagc taaccagcaa ttcttagtct actgtgaaat cgatgggtct | 780 |
| ggaaatggat ggactgtgtt tcagaagaga cttgatggca gtgtagattt caagaaaaac | 840 |
| tggattcaat ataagaagg atttggacat ctgtctccta ctggcacaac agaattttgg | 900 |
| ctggaaatg agaagattca tttgataagc acacagtctg ccatcccata tgcattaaga | 960 |
| gtggaactgg aagactggaa tggcagaacc agtactgcag actatgccat gttcaaggtg | 1020 |
| ggacctgaag ctgacaagta ccgcctaaca tatgccctact tcgctggtgg ggatgctgga | 1080 |
| gatgcctttg atggctttga ttttggcgat gatcctagtg acaagttttt cacatcccat | 1140 |
| aatggcatgc agttcagtac ctgggacaat gacaatgata gtttgaagg caactgtgct | 1200 |
| gaacaggatg gatctggttg gtggatgaac aagtgtcacg ctggccatct caatggagtt | 1260 |
| tattaccaag gtggcactta ctcaaaagca tctactccta atggttatga taatggcatt | 1320 |
| atttgggcca cttggaaaac ccggtggtat tccatgaaga aaccactat gaagataatc | 1380 |
| ccattcaaca gactcacaat ggagaagga cagcaacacc acctgggggg agccaaacag | 1440 |
| gctggagacg tttaaaagac cgtttcaaaa gagatttact tttttaaagg actttatctg | 1500 |
| aacagagaga tataatattt ttcctattgg acaatggact tgcaaagctt cacttcattt | 1560 |
| taagagcaaa agaccccatg ttgaaaactc cataacagtt ttatgctgat gataaatttat | 1620 |
| ctacatgcat ttcaataaac cttttgtttc ctaagactag aaaaa | 1665 |

<210> SEQ ID NO 10
<211> LENGTH: 1763
<212> TYPE: DNA
<213> ORGANISM: Homo sapiens

<400> SEQUENCE: 10

| | |
|---|---|
| cttctggtaa ggaggccccg tgatcagctc cagccatttg cagtcctggc tatcccagga | 60 |
| gcttacataa agggacaatt ggagcctgag aggtgacagt gctgacacta caaggctcgg | 120 |
| agctccgggc actcagacat catgagttgg tccttgcacc cccggaattt aattctctac | 180 |
| ttctatgctc tttattttct ctcttcaaca tgtgtagcat atgttgctac cagagacaac | 240 |
| tgctgcatct tagatgaaag attcggtagt tattgtccaa ctacctgtgg cattgcagat | 300 |
| ttcctgtcta cttatcaaac caaagtagac aaggatctac agtctttgga agacatctta | 360 |
| catcaagttg aaaacaaaac atcagaagtc aaacagctga taaaagcaat ccaactcact | 420 |
| tataatcctg atgaatcatc aaaaccaaat atgatagacg ctgctacttt gaagtccagg | 480 |
| aaaatgttag aagaaattat gaaatatgaa gcatcgattt taacacatga ctcaagtatt | 540 |
| cgatatttgc aggaaatata taattcaaat aatcaaaaga ttgttaacct gaaagagaag | 600 |
| gtagcccagc ttgaagcaca gtgccaggaa ccttgcaaag acacggtgca aatccatgat | 660 |
| atcactggga aagattgtca agacattgcc aataagggag ctaaacagag cgggctttac | 720 |
| tttattaaac ctctgaaagc taaccagcaa ttcttagtct actgtgaaat cgatgggtct | 780 |
| ggaaatggat ggactgtgtt tcagaagaga cttgatggca gtgtagattt caagaaaaac | 840 |

-continued

```
tggattcaat ataaagaagg atttggacat ctgtctccta ctggcacaac agaattttgg      900
ctgggaaatg agaagattca tttgataagc acacagtctg ccatcccata tgcattaaga      960
gtggaactgg aagactggaa tggcagaacc agtactgcag actatgccat gttcaaggtg     1020
ggacctgaag ctgacaagta ccgcctaaca tatgcctact tcgctggtgg ggatgctgga     1080
gatgcctttg atggctttga ttttggcgat gatcctagtg acaagttttt cacatcccat     1140
aatggcatgc agttcagtac ctgggacaat gacaatgata agtttgaagg caactgtgct     1200
gaacaggatg gatctggttg gtggatgaac aagtgtcacg ctggccatct caatggagtt     1260
tattaccaag gtggcactta ctcaaaagca tctactccta atggttatga taatggcatt     1320
atttgggcca cttggaaaac ccggtggtat tccatgaaga aaaccactat gaagataatc     1380
ccattcaaca gactcacaat tggagaagga cagcaacacc acctgggggg agccaaacag     1440
gtcagaccag agcaccctgc ggaaacagaa tatgactcac tttaccctga ggatgatttg     1500
tagaaaatta actgctaact tctattgacc cacaaagttt cagaaattct ctgaaagttt     1560
cttccttttt tctcttacta tatttattga tttcaagtct tctattaagg acatttagcc     1620
ttcaatggaa attaaaactc atttaggact gtatttccaa attactgata tcagagttat     1680
ttaaaaattg tttatttgag gagataacat ttcaactttg ttcctaaata tataataata     1740
aaatgattga ctttatttgc aaa                                              1763
```

BLOOD BIOMARKERS FOR NECROTIZING ENTEROCOLITIS

CROSS-REFERENCE TO RELATED APPLICATIONS

This application claims priority to the filing date of U.S. Provisional Patent Application Ser. No. 61/657,577 filed Jun. 8, 2012, the full disclosure of which is incorporated herein by reference.

STATEMENT REGARDING FEDERALLY SPONSORED RESEARCH

This invention was made with Government support under contract RR025742 awarded by the National Institutes of Health. The Government has certain rights in this invention.

INCORPORATION BY REFERENCE OF SEQUENCE LISTING

A Sequence Listing is provided herewith as a text file, "STAN-934WO SeqList_ST25.txt" created on Jun. 3, 2013 and having a size of 45 KB. The contents of the text file are incorporated by reference herein in their entirety.

FIELD OF THE INVENTION

This invention pertains to the fields of necrotizing enterocolitis and sepsis.

BACKGROUND OF THE INVENTION

Necrotizing enterocolitis (NEC), intestinal perforation (IP) and sepsis are three life-threatening gastrointestinal diseases among neonates and together constitute a leading cause of overall morbidity and mortality in premature newborns. However, there is considerable overlap in the early clinical presentation of NEC, IP and sepsis in newborns. Furthermore, while half of NEC-affected infants will recover with medical therapy alone (the M-class), 30-50% develop a progressive form of the disease (Progressive Necrotizing Enterocolitis) that requires surgery (the S-class) to prevent mortality. Currently utilized clinical parameters including laboratory tests and diagnostic imaging fail to capture the nuanced differences between these entities during their onset and progression. Protein biomarkers detectable in clinically available specimens would provide the needed molecular diagnostic and prognostic "fingerprint" against which we can begin to measure various interventions. Such biomarkers could be used to improved methods for diagnostic and prognostic class prediction in NEC, IP and sepsis, and to improve predictions on responsiveness to known and new therapies. The present invention addresses these issues.

Publications

U.S. Application No. 2009/0191551 teaches using the level of secretor antigens in a biological fluid as a marker to predict the risk of developing NEC. Thuijls G, et al. (2010) *Non-invasive markers for early diagnosis and determination of the severity of necrotizing enterocolitis*. Ann Surg. 251 (6):1174-80, discusses using I-FABP and claudin-3 protein levels in urine and calprotectin protein levels in fecal matter as diagnostic markers of NEC, and I-FABP protein levels in urine as a prognostic marker of disease severity. Evennett N, et al. (2009) *A systematic review of serologic tests in the diagnosis of necrotizing enterocolitis*. J Pediatr Surg. 44(11): 2192-201 is a review of publications that were deemed by the authors to be potentially relevant to diagnostic performance of serological tests in NEC. Young C, et al. (2009) *Biomarkers for infants at risk for necrotizing enterocolitis: clues to prevention?* Pediatr Res. 65(5 Pt 2):91R-97R is a review that discusses the potential value of genomic and proteomic studies of NEC in the identification of biomarkers for early diagnosis and targeted prevention of this disease.

SUMMARY OF THE INVENTION

Necrotizing Enterocolitis (NEC) biomarkers, NEC biomarker panels, and methods for obtaining a NEC signature for a sample are provided. Also provided are methods, compositions, and kits for making a Necrotizing Enterocolitis (NEC) assessment of an individual, e.g. for diagnosing NEC in a patient, prognosing NEC in a patient, treating an NEC patient, etc. These methods find use in a number of applications, such as diagnosing and treating infants who are suspected of having NEC, intestinal perforation (IP), or sepsis.

In some aspects of the disclosure, methods are provided for diagnosing NEC in a patient. In some aspects of the disclosure, methods are provided for diagnosing NEC requiring surgery (NEC-S) in a patient. In some aspects of the invention, methods are provided for predicting responsiveness of an NEC patient to a medical intervention. In some aspects of the invention, methods are provided for treating an NEC patient.

In some embodiments, an NEC biomarker signature (e.g., an NEC diagnostic biomarker signature, an NEC-S diagnostic biomarker signature) is obtained for a patient, where an NEC biomarker signature comprises the quantitative data on the biomarker level of one or more NEC biomarkers, i.e. biomarkers that are expressed at either elevated or depressed levels (or exhibit increased or decreased protein activity) in NEC and/or NEC-S patients versus unaffected individuals. The NEC biomarker signature of the patient can then be compared to an NEC biomarker signature from a reference sample, and the results of this comparison can be employed to provide an NEC diagnosis to the patient. In some embodiments, the patient is suspected of having NEC, intestinal perforation (IP), or sepsis prior to diagnosis.

In some embodiments, the NEC biomarker signature is obtained by measuring the amount of protein in a body fluid that is encoded by one or more NEC biomarkers to arrive at an NEC protein signature. In some embodiments, the body fluid is blood (e.g., whole blood, fractionated blood, plasma, serum, etc.). In some embodiments, the one or more NEC biomarkers is selected from the group of NEC-Dx biomarkers consisting of: Factor XIII (FXIII) biomarker, and Fibrinogen gamma chain (FGG) dimer, where decreased levels of FXIII protein activity, FXIII protein, and/or FGG is diagnostic for NEC. In some embodiments, the one or more NEC biomarkers is selected from the group of NEC-S-Dx biomarkers consisting of: Alpha-2-macroglobulin (A2M), Angiotensinogen (AGT), and Hemopexin (HPX), where elevated levels of AGT and decreased levels A2M and HPX is diagnostic for NEC-S. In some embodiments elevated levels of AGT is diagnostic for NEC-S. In some embodiments decreased levels of A2M is diagnostic for NEC-S. In some embodiments decreased levels of HPX is diagnostic for NEC-S. In some embodiments elevated levels of AGT and decreased levels of A2M is diagnostic for NEC-S. In some embodiments elevated levels of AGT and decreased levels of HPX is diagnostic for NEC-S. In some embodiments, decreased levels of both A2M and HPX is diagnostic for NEC-S.

In some embodiments, the method further comprises obtaining an NEC clinical score. In such embodiments, the NEC biomarker signature and NEC clinical score can be compared to an NEC biomarker signature and NEC clinical score from a reference sample, and the results of both comparisons can be employed to provide an NEC assessment.

BRIEF DESCRIPTION OF THE DRAWINGS

It is emphasized that, according to common practice, the various features of the drawings are not to-scale. On the contrary, the dimensions of the various features are arbitrarily expanded or reduced for clarity. Included in the drawings are the following figures.

FIG. 2 presents the patient demographics of the patients used in the studies presented here.

FIG. 7 depicts the comparison of A2M, AGT, and HPX protein levels in normal, NEC-M, NEC-S, and sepsis patients.

FIG. 8 presents the Mann Whitney test P values for protein levels in normal, NEC-M, NEC-S, and sepsis patients.

FIG. 15 depicts the amino acid sequence and nucleic acid sequence of human AGT.

FIG. 16 depicts the amino acid sequence and nucleic acid sequence of human HPX.

FIG. 17 depicts the amino acid sequence of human A2M.

FIG. 18 depicts the nucleic acid sequence of human A2M.

FIG. 19 depicts the amino acid sequences of human FGG isoforms gamma-A and gamma-B.

FIG. 20 depicts the nucleic acid sequence of human FGG isoform gamma-A.

FIG. 21 depicts the nucleic acid sequence of human FGG isoform gamma-B.

DETAILED DESCRIPTION OF THE INVENTION

Figure 1:
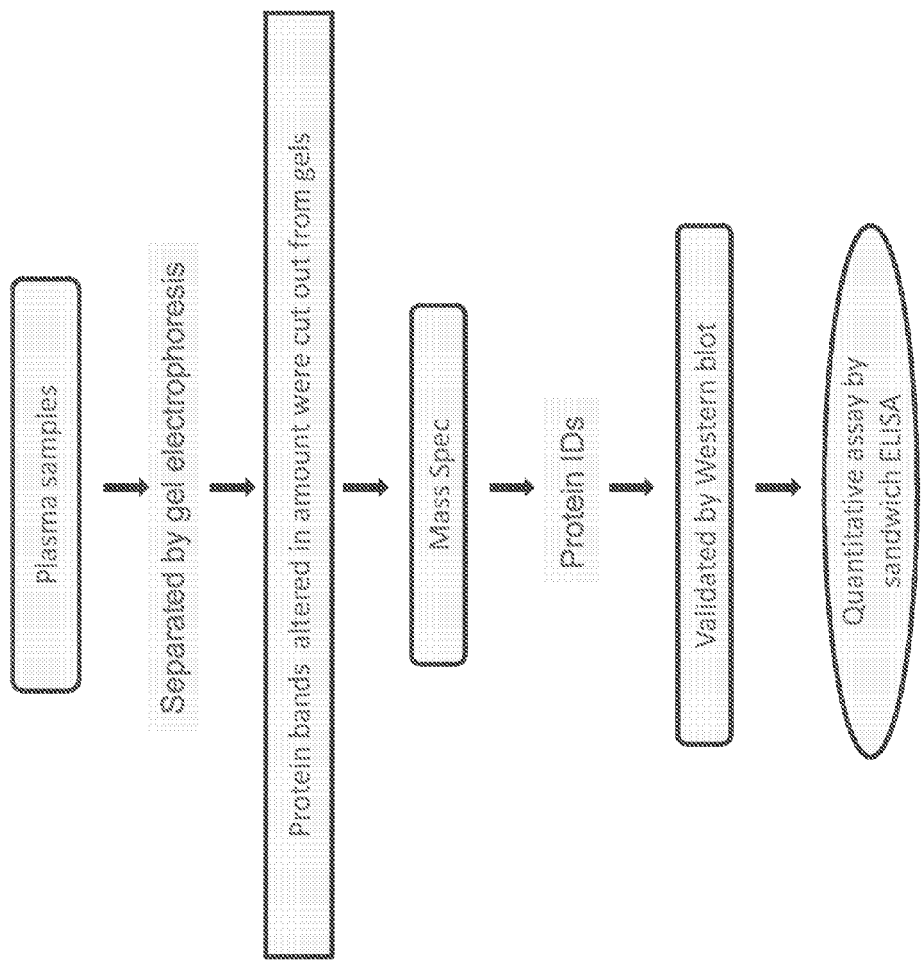
FIG. 1 depicts the study design for discovery of NEC biomarkers (NEC-S-Dx biomarkers).

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "Necrotizing Enterocolitis," or "NEC," is used herein to describe the gastrointestinal condition in which a segment of the intestine becomes necrotic; in some instances, the intestinal region perforates, causing peritonitis and often free intra-abdominal air. Infection and inflammation of the gut are hallmarks of the condition, along with abdominal distention, blood in the stool, diarrhea, feeding intolerance, lethargy, temperature instability, and vomiting. In some instances, the NEC may be further classified as NEC-M, for "medical", class; or NEC-S, for "surgical", class.

The terms "medical class NEC", "M class NEC", "NEC-M", or "non-progressive NEC" are used interchangeably herein to describe the class of NEC that is typically responsive to medical therapies, e.g. stage I, stage II, and in some instances stage III of Bell's criteria (Table 1 below). Medical therapy includes, for example, broad spectrum antibiotics for 3-14 days, accompanied intravenous fluids, total parenteral fluids (TPN) and NPO (nothing by mouth).

The terms "surgical class NEC", "S class NEC", "NEC-S", "S-class", or "progressive NEC" are used interchangeably herein to describe the class of NEC that requires surgical intervention, e.g. stage IIIB of Bell's criteria (Table 1 below). As such, "diagnosing NEC-S in a patient" or "making an NEC-S diagnosis for a patient" refers to the determination of whether a patient is an NEC-S patient (i.e., a patient with NEC that requires surgery or a patient with NEC requiring surgery). In this surgery, gangrenous bowel is resected, and ostomies for intestinal stream diversion are created. With resolution of sepsis and peritonitis, intestinal continuity can be reestablished several weeks or months later.

The terms "focal intestinal perforation" (FIP), "spontaneous intestinal perforation" (SIP), or "intestinal perforation" (IP) are used interchangeably herein to describe an isolated intestinal perforation that, unlike NEC, is not accompanied by gross necrosis of the tissue. In FIP, the gestational age is significantly lower than in NEC (approx. 24 weeks versus 27 weeks for NEC), the incidence of coexistent respiratory distress syndrome (RDS) is higher (88% versus 37% for NEC), and the age of onset is younger (approx. 7.3 days versus approx. 7.9 days for NEC). See, e.g. Okuyama et al. (2002) Pediatr Surg Int 18:704-706, the disclosure of which is herein incorporated by reference.

The term "sepsis" is used herein to describe a bacterial infection in the context of fever of greater than 38° C. (100.4° F.). Blood pressure drops, resulting in shock. Major organs and systems, including the kidneys, liver, lungs, and central nervous system, stop functioning normally. Infection is typically confirmed by a blood culture that reveals bacteria, blood gases that reveal acidosis, kidney function tests that are abnormal, a platelet count that is lower than normal, and/or a white blood cell count that is lower or higher than normal. Other indications of sepsis include a blood differential that shows immature white blood cells, the presence of higher than normal amounts of fibrin degradation products in the blood, and a peripheral smear that shows a low platelet count and destruction of red blood cells. The treatment is typically antibiotics delivered intravenously. In infants, sepsis may be classified as "early onset" (within the first 7 days of birth), which usually results from organisms acquired intrapartum, and "late onset" (more than 7 days after birth), in which the infection is usually by organisms from the environment.

A "disease assessment" or "disorder assessment", e.g., an "NEC assessment", as used herein generally includes a prediction of a subject's susceptibility to a disease or disorder (e.g., NEC), a determination as to whether a subject is presently affected by a disease or disorder, a prognosis of a subject affected by a disease or disorder (e.g., identification of disease states, stages of the disease, prediction of responsiveness to a therapy and/or intervention, e.g. a medical or surgical therapy and/or intervention, likelihood that a patient will die from the disease, etc.), and the use of therametrics (e.g., monitoring a subject's condition to provide information as to the effect or efficacy of therapy). Thus, for example, an NEC assessment may be used to diagnose, prognose, or treat an NEC condition. Thus, the term "NEC assessment" as used herein generally encompasses making a NEC diagnosis (e.g., a determination of whether a patient has NEC, a determination of whether a patient has NEC-S or NEC-M, etc.) and also encompasses a prediction of responsiveness to NEC medical intervention (e.g., an NEC prognosis, a prediction of whether an NEC patient (i.e., a patient with NEC) will be responsive to NEC medical intervention, etc.).

By "making an NEC diagnosis," it is generally meant making a NEC determination, e.g. a determination as to whether a subject (e.g. a subject that has clinical symptoms of NEC, a subject that is asymptomatic for NEC but has risk factors associated with NEC, a subject that is asymptomatic for NEC and has no risk factors associated with NEC) is presently affected by NEC (i.e. diagnosing NEC); a classification of the subject's NEC into a subtype of the disease or disorder, e.g. NEC-S or NEC-M (i.e. diagnosing NEC-S); a determination of the severity of NEC; and the like. By "prognosing" a NEC, or "making an NEC prognosis," it is generally meant making a NEC prediction, e.g. a prediction of a subject's susceptibility, or risk, of developing NEC; a prediction of the course of NEC progression and/or NEC outcome, e.g. expected onset of the NEC, expected duration of the NEC, expectations as to whether the NEC-M will develop into NEC-S, etc.; a prediction of a subject's responsiveness to medical intervention or surgery for the NEC, i.e. an NEC-S diagnosis, e.g., positive response, a negative response, no response at all; and the like. By "monitoring" an NEC, it is generally meant monitoring a subject's condition, e.g. to inform a NEC diagnosis, to inform a NEC prognosis, to provide information as to the effect or efficacy of a NEC treatment, and the like. By "treating" a NEC it is meant prescribing or providing any treatment of a NEC in a mammal, and includes: (a) preventing the NEC from occurring in a subject which may be predisposed to NEC but has not yet been diagnosed as having it; (b) inhibiting the NEC, i.e., arresting its development; or (c) relieving the NEC, i.e., causing regression of the NEC.

By a disease "biomarker" or disease "marker" it is meant a molecular entity whose representation in a sample is associated with a disease phenotype. In other words, the marker may be said to be differentially represented in a sample having a disease phenotype. Differential representation may be measured by any of a number of well-known methods in the art. For example, differential representation may be measured by measuring the expression level, i.e. amount or concentration, of gene product (i.e., protein or RNA), where the gene product is differentially expressed (i.e., expressed at a higher or lower level) among patients with the disease relative to patients without the disease or with a different class of the disease. As another example, differential representation may be measured by measuring the activity level of the marker, e.g. its enzymatic activity, e.g. its cleavage activity, its phosphorylation activity, etc.

By a disease "biomarker panel" or disease "marker panel" it is meant a collection, or combination, of molecular entities, e.g. two or more, three or more, four or more, five or more entities, whose representation in a sample is associated with a disease phenotype. Accordingly, by an NEC biomarker panel (i.e., a panel of NEC biomarkers) it is meant a collection of NEC biomarkers (e.g., two or more, three or more, four or more, five or more, etc.) whose representation (level of protein, level of protein activity, level of RNA, etc.), when considered individually and/or in combination, find use in obtaining a NEC signature.

By "biomarker signature" or "biomarker panel signature" it is meant a representation of the measured level/activity (e.g., protein level, protein activity level, RNA level, etc.) of a biomarker or combination of biomarkers of interest. A biomarker signature or biomarker panel signature typically comprises the quantitative data on the biomarker levels/activity of these one or more biomarkers of interest. Examples of biomarker signatures include collections of measured protein, protein activity, and/or RNA levels. For example, a "protein biomarker signature" comprises the quantitative data on the amount of polypeptide encoded by one or more NEC biomarkers. An "activity biomarker signature" comprises the quantitative data on the amount of protein activity (e.g., enzymatic activity as determined by an assay), exhibited by one or more NEC biomarkers. An "RNA biomarker signature" comprises the quantitative data on the amount of RNA transcribed by one or more NEC biomarkers. As used herein, the term "biomarker signature" encompasses "protein signature", "activity signature", as well as "RNA signature." Examples of biomarker signatures include biomarker profiles and biomarker scores. By a "biomarker profile" it is meant the normalized representation of one or more biomarkers of interest, more usually two or more biomarkers of interest, i.e. a panel of biomarkers of interest, in a patient sample. In some instances, the biomarker signature may be a biomarker score. By a "biomarker score" it is meant a single metric value that represents the sum of the weighted representations of one or more biomarkers of interest, more usually two or more biomarkers of interest, in a patient sample. Biomarker profiles and scores are discussed in greater detail below.

The term "sample" with respect to a patient encompasses blood and other liquid samples of biological origin, solid tissue samples such as a biopsy specimen or tissue cultures or cells derived or isolated therefrom and the progeny thereof. The definition also includes samples that have been manipulated in any way after their procurement, such as by treatment with reagents; washed; or enrichment for certain cell populations. The definition also includes samples that have been enriched for particular types of molecules, e.g., nucleic acids, polypeptides, etc.

The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. The term "blood sample" encompasses a blood sample (e.g., peripheral blood sample) and any derivative thereof (e.g., fractionated blood, plasma, serum, etc.).

The term "risk classification" means a level of risk (or likelihood) that a subject will experience a particular clinical outcome. A subject may be classified into a risk group or classified at a level of risk based on the methods of the present disclosure, e.g. high, medium, or low risk. A "risk group" is a group of subjects or individuals with a similar level of risk for a particular clinical outcome. Examples of NEC risk groups include M-class and the S-class.

The term "hazard ratio" means the effect of an explanatory variable on the hazard, or risk, of an event occurring. For example, using a Cox proportional hazards regression model, if a variable, e.g. an LSC score, is prognostic, its hazard rate is different in patients with a particular prognosis relative to the hazard rate of other subclasses, and the hazard ratio of the gene is not equal to 1.

The terms "individual," "subject," "host," and "patient," are used interchangeably herein and refer to any mammalian subject for whom diagnosis, treatment, or therapy is desired, particularly humans.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

Necrotizing Enterocolitis (NEC) biomarkers, NEC biomarker panels, and methods for obtaining a NEC signature for a sample are provided. Also provided are methods, compositions, and kits for making a Necrotizing Enterocolitis (NEC) assessment of an individual, e.g. for diagnosing NEC in a patient, prognosing NEC in a patient, treating an NEC patient, etc. These methods find use in a number of applications, such as diagnosing and treating infants who are suspected of having NEC, intestinal perforation (IP), or sepsis. These and other objects, advantages, and features of the invention will become apparent to those persons skilled in the art upon reading the details of the compositions and methods as more fully described below.

In describing the subject invention, compositions useful for making a NEC assessment will be described first, followed by methods, systems and kits for their use.

NEC Biomarkers and Biomarker Panels

In some aspects of the invention, NEC biomarkers and panels of NEC biomarkers are provided. By an "NEC biomarker" or "NEC marker" it is meant a molecular entity whose representation in a sample is associated with a NEC phenotype. For example, a NEC marker may be differentially represented, e.g. as measured by concentration, by activity, etc. in a sample from an individual that will develop or has developed NEC as compared to a healthy individual. For example, the marker may be differentially represented (e.g, expressed (e.g., protein, RNA) at a higher or lower level, exhibiting higher or lower activity, etc.) among patients with any form of NEC (e.g., NEC, NEC-S, NEC-M, etc.) relative to patients without NEC or to patients with a different form of NEC. For example, the concentration or activity of marker in a sample may be 1.5-fold, 2-fold, 2.5-fold, 3-fold, 4-fold, 5-fold, 7.5-fold, 10-fold, or greater in a sample associated with the NEC phenotype than in a sample not associated with the NEC phenotype. In other instances, a reduced level of marker is associated with the NEC phenotype. For example, the concentration or activity of marker in a sample may be 10% less, 20% less, 30% less, 40% less, 50% less or more in a sample associated with the NEC phenotype than in a sample not associated with the NEC phenotype. Accordingly, NEC biomarkers may be used to diagnose whether a patient has NEC (i.e., whether the patient is an NEC patient); used to determine whether a patient is an NEC patient with a subclass of NEC (e.g., whether the patient is an NEC-S or NEC-M patient); used to determine a differential diagnosis (e.g., determine an NEC prognosis, i.e., determine whether an NEC patient is likely to respond to NEC medical intervention, etc.); and the like. The term "NEC biomarker" encompasses NEC-Dx biomarkers and NEC-S-Dx biomarkers, both of which are described in more detail below.

NEC biomarkers may include proteins associated with NEC and their corresponding genetic sequences, i.e. mRNA, DNA, etc. By a "gene" or "recombinant gene" it is meant a nucleic acid comprising an open reading frame that encodes for the protein. The boundaries of a coding sequence are determined by a start codon at the 5' (amino) terminus and a translation stop codon at the 3' (carboxy) terminus. A transcription termination sequence may be located 3' to the coding sequence. In addition, a gene may optionally include its natural promoter (i.e., the promoter with which the exons and introns of the gene are operably linked in a non-recombinant cell, i.e., a naturally occurring cell), and associated regulatory sequences, and may or may not have sequences upstream of the AUG start site, and may or may not include untranslated leader sequences, signal sequences, downstream untranslated sequences, transcriptional start and stop sequences, polyadenylation signals, translational start and stop sequences, ribosome binding sites, and the like. The term "gene product" or "expression product" are used herein to refer to the RNA transcription products (transcripts) of the gene, including mRNA, and the polypeptide translation products of such RNA transcripts. A gene product can be, for example, an unspliced RNA, an mRNA, a splice variant mRNA, a microRNA, a fragmented RNA, a polypeptide, a post-translationally modified polypeptide, a splice variant polypeptide, etc. The term "RNA transcript" as used herein refers to the RNA transcription products of a gene, including, for example, mRNA, an unspliced RNA, a splice variant mRNA, a microRNA, and a fragmented RNA. The term "polypeptide" as used herein refers to the amino acid product encoded by a gene, including, for example, full length gene product, splice variants of the full length gene product, and fragments of the gene product, e.g. peptides.

As demonstrated in the examples of the present disclosure, the inventors have identified a number of molecular entities whose differential representation, e.g. expression and/or activity level, are associated with NEC or particular subtypes of NEC and thus, that find use either alone or in combination (i.e. as a biomarker panel) in providing a NEC assessment, e.g. diagnosing NEC, prognosing NEC, monitoring a subject with NEC, determining a treatment for a subject affected with NEC, and the like. These biomarkers include, but are not limited to, Factor XIII (FXIII), Fibrinogen gamma chain (FGG) dimer, Angiotensinogen (AGT), Hemopexin (HPX), and Alpha-2-macroglobulin (A2M). The inventors of the present disclosure have discovered that reduced representation of Factor XIII in a sample are diagnostic of a patient having NEC.

By "Fibrinogen gamma chain," or "FGG" it is meant (i) a polypeptide comprising an amino acid sequence having an amino acid sequence identity of 90% or more (e.g., 92% or more, 95% or more, 96% or more, 97% or more, 98% or more, 99% or more, 99.5% or more, or 100%) to the amino acid sequence set forth in one of SEQ ID NOs: 7 and 8 (there are two isoforms); and/or (ii) a polynucleotide comprising a nucleotide sequence having a nucleic acid sequence identity of 90% or more (e.g., 92% or more, 95% or more, 96% or more, 97% or more, 98% or more, 99% or more, 99.5% or more, or 100%) to the nucleic acid sequence set forth in one of SEQ ID NOs: 9 and 10 (there are two isoforms). FGG encodes the gamma component of fibrinogen.

In the presence of the transglutaminase activity of FXIII (see below), FGG undergoes intermolecular covalent cross-linking to form dimers. As demonstrated in the working examples below, the inventors of the present disclosure have discovered that reduced, or decreased, representation of FGG dimers in a sample is diagnostic of NEC. Thus, FGG dimers may be considered to be biomarkers, and FGG dimerization (i.e., dimer formation) can be considered to represent a readout of FXIII transglutaminase activity. FGG dimer biomarkers in a sample may be detected by any convenient method known by one of ordinary skill in the art (e.g., SDS-PAGE (sodium dodecyl sulfate polyacrylamide gel electrophoresis), followed by Western blotting with an anti-FGG antibody). For an example of FGG dimer detection, see FIG. 12. For more information about FGG dimers, see for example, Siebenlist et al, J Biol Chem. 1994 Nov. 11; 269(45):28414-9, which is hereby incorporated by reference in its entirety.

By "Factor XIII (FXIII)" it is meant the transglutaminase that circulates in the plasma as a heterotetramer of two catalytic A subunits and two carrier B subunits (A2B2). It is activated by thrombin into Factor XIIIa, which requires calcium as a cofactor. Cleavage by thrombin between residue Arg37 and Gly38 on the N-terminus of the A subunit, leads to the release of the activation peptide (MW 4000 da). In the presence of calcium the carrier subunits dissociate from the catalytic subunits, leading to a three dimensional change in conformation of FXIII and hence the exposure of catalytic cysteine residue. Dimer formation of Fibrinogen gamma chain (FGG) is catalyzed by Factor XIIIa (FXIIIa) transglutaminase activity. As demonstrated in the working examples below, the inventors of the present disclosure have discovered that reduced levels of FXIII protein and reduced FXIII protein activity (transglutaminase activity) are diagnostic of NEC.

By "Angiotensinogen" or "AGT" it is meant (i) a polypeptide comprising an amino acid sequence having an amino acid sequence identity of 90% or more (e.g., 92% or more, 95% or more, 96% or more, 97% or more, 98% or more, 99% or more, 99.5% or more, or 100%) to the amino acid sequence set forth in SEQ ID NO: 1; and/or (ii) a polynucleotide comprising a nucleotide sequence having a nucleic acid sequence identity of 90% or more (e.g., 92% or more, 95% or more, 96% or more, 97% or more, 98% or more, 99% or more, 99.5% or more, or 100%) to the nucleic acid sequence set forth in SEQ ID NO: 4. The inventors of the present disclosure have discovered that an increased representation of AGT in a blood sample correlates with a prognosis that a patient has NEC-S (a class of NEC requiring surgery, i.e., the patient is unlikely to respond to medical intervention).

By "Hemopexin" or "HPX" it is meant (i) a polypeptide comprising an amino acid sequence having an amino acid sequence identity of 90% or more (e.g., 92% or more, 95% or more, 96% or more, 97% or more, 98% or more, 99% or more, 99.5% or more, or 100%) to the amino acid sequence set forth in SEQ ID NO: 2; and/or (ii) a polynucleotide comprising a nucleotide sequence having a nucleic acid sequence identity of 90% or more (e.g., 92% or more, 95% or more, 96% or more, 97% or more, 98% or more, 99% or more, 99.5% or more, or 100%) to the nucleic acid sequence set forth in SEQ ID NO: 5. The inventors of the present disclosure have discovered that a reduced, or decreased, representation of HPX in a blood sample correlates with a prognosis that a patient has NEC-S.

By "Alpha-2-macroglobulin" or "A2M" it is meant (i) a polypeptide comprising an amino acid sequence having an amino acid sequence identity of 90% or more (e.g., 92% or more, 95% or more, 96% or more, 97% or more, 98% or more, 99% or more, 99.5% or more, or 100%) to the amino acid sequence set forth in SEQ ID NO: 3; and/or (ii) a polynucleotide comprising a nucleotide sequence having a nucleic acid sequence identity of 90% or more (e.g., 92% or more, 95% or more, 96% or more, 97% or more, 98% or more, 99% or more, 99.5% or more, or 100%) to the nucleic acid sequence set forth in SEQ ID NO: 6. The inventors of the present disclosure have discovered that a reduced, or decreased, representation of A2M in a blood sample correlates with a prognosis that a patient has NEC that is treatable only by surgical methods. The inventors of the present disclosure have discovered that a reduced, or decreased, representation of A2M in a blood sample correlates with a prognosis that a patient has NEC-S.

In some embodiments, one or more of the above-mentioned biomarkers finds use in determining if an individual has NEC. In such instances, the biomarker or panel of biomarkers may be referred to as a "NEC diagnostic biomarker" or "NEC-Dx biomarker" and "NEC diagnostic panel" or "NEC-Dx panel" Exemplary NEC-Dx biomarkers whose representation (e.g., concentration, level of activity) is altered in patients with NEC compared to patients without NEC include, but are not limited to: Factor XIII (FXIII) (e.g., FXIII activity level (i.e., FXIII transglutaminase activity level), FXIII protein level, etc.); and Fibrinogen gamma chain (FGG) dimer (i.e., the amount of FGG dimer present).

In some embodiments, one or more of the above-mentioned biomarkers finds use in prognosing NEC. That is, one or more of the above-mentioned biomarkers may find use in determining if the NEC patient will be responsive to medical treatment or will require surgery, i.e. diagnosing NEC-S. In such instances, the biomarker or panel of biomarkers may be referred to as a "NEC-prognostic biomarker", "NEC-S diagnostic biomarker", or "NEC-S-Dx biomarker," and a "NEC prognostic panel" or "NEC-S diagnostic panel" or "NEC-S-Dx panel". Exemplary NEC-S-Dx biomarkers whose representation (e.g., concentration, level of activity) is altered in patients with NEC-S as compared to patients with NEC-M, with sepsis, or with IP include, but are not limited to: Angiotensinogen (AGT), Hemopexin (HPX), Alpha-2-macroglobulin (A2M), and combinations thereof.

Methods

In some aspects of the invention, methods are provided for obtaining an NEC biomarker signature (e.g. an NEC-S-Dx biomarker signature, an NEC-Dx biomarker signature, etc) for a patient (e.g., a patient that is suspected of having NEC or sepsis).

As discussed above, a "biomarker signature" is a representation of the measured level/activity (e.g., protein level, protein activity level, RNA level, etc.) of a biomarker or combination of biomarkers of interest in a patient sample, and typically comprises quantitative data on the expression levels/activity of those one or more proteins in that sample. As such, an "NEC biomarker signature" is a representation of the expression levels or activity of one or more NEC biomarkers, and comprises the quantitative data on the expression levels and/or activity level of these one or more biomarkers. In certain embodiments, the NEC biomarker signature is an "NEC protein biomarker signature", i.e. it comprises the quantitative data on the amount of polypeptide encoded by one or more NEC biomarkers. In certain embodiments, the NEC biomarker signature is an "NEC activity signature", i.e. it comprises the quantitative data on the amount of protein activity (e.g., enzymatic activity as determined by an assay), exhibited by one or more NEC biomarkers. In certain embodiments, the NEC biomarker signature is an "NEC RNA signature", i.e. it comprises the quantitative data on the amount of RNA transcribed by one or more NEC biomarkers.

For example, in some embodiments, the subject methods may be used to obtain an "NEC diagnostic signature" (also referred to herein as "NEC-Dx signature", or "NEC-Dx biomarker signature"); that is, the subject methods may be used to obtain a representation of the expression levels or activity of one or more NEC-Dx biomarkers that are up- or down-regulated (i.e., expressed at a higher or lower level, exhibits a higher or lower level of activity, etc.), in NEC patients relative to patients without NEC, e.g. healthy individuals, individuals with sepsis, etc. In certain embodiments, the NEC diagnostic signature is an "NEC diagnostic protein signature" or "NEC-Dx protein signature", comprising the quantitative data on the amount of polypeptide encoded by one or more NEC-Dx biomarkers. In certain embodiments, the NEC diagnostic signature is a "NEC diagnostic activity signature" or "NEC-Dx activity signature", comprising the quantitative data on the amount of protein activity (e.g., enzymatic activity as determined by an assay), exhibited by one or more NEC-Dx biomarkers. In certain embodiments, the NEC diagnostic signature is a "NEC diagnostic RNA signature" or "NEC-Dx RNA signature", comprising the quantitative data on the amount of RNA transcribed by one or more NEC-Dx biomarkers. As used herein, The term "NEC-Dx biomarker signature" encompasses "NEC-Dx protein signature", "NEC-Dx activity signature", as well as "NEC-Dx RNA signature." Exemplary NEC-Dx biomarkers that are reduced in patients with NEC compared to patients without NEC include: Factor XIII (FXIII) (e.g., FXIIIa transglutaminase activity, FXIII protein levels) and Fibrinogen gamma chain (FGG) dimers (i.e., the amount of FGG dimer present, e.g., relative to a non-dimerized form, relative to a control protein, etc.).

As another example, in some embodiments, the subject methods may be used to obtain an "NEC-S diagnostic biomarker signature" (also referred to herein as a NEC biomarker prognostic signature, or "NEC-S-Dx biomarker signature"); that is, the subject methods may be used to obtain a representation of the expression levels of one or more NEC-S-Dx biomarkers (e.g., proteins), and comprises the quantitative data on the expression levels of these one or more NEC-S-Dx biomarkers. In certain embodiments, the NEC-S diagnostic signature is an "NEC-S diagnostic protein signature" or "NEC-S-Dx protein signature", i.e. it comprises the quantitative data on the amount of polypeptide encoded by one or more NEC-S-Dx biomarkers and/or peptides thereof. In certain embodiments, the NEC-S diagnostic signature is an "NEC-S diagnostic RNA signature" or "NEC-S-Dx RNA signature", i.e. it comprises the quantitative data on the amount of RNA transcribed by one or more NEC-S-Dx biomarkers. The term "NEC-S-Dx biomarker signature" encompasses "NEC-S-Dx protein signature" as well as "NEC-S-Dx RNA signature." Non-limiting examples of NEC-S-Dx biomarkers are provided in Table 1 below.

TABLE 1

NEC-S-Dx biomarkers. Sequences for genes are provided as NCBI reference sequences, the disclosures of which are specifically incorporated herein by reference. NCBI Reference Sequences are listed as "protein, nucleic acid." SEQ ID numbers are listed as "protein, nucleic acid".

| Class | Gene | Gene name, aliases | NCBI Reference Sequence | SEQ ID NO: |
|-------|------|--------------------|-----|-----|
| NEC-S | AGT | angiotensinogen (serpin peptidase inhibitor, clade A, member 8) | NP_000020.1, NM_000029.3 | 1, 4 |
| | HPX | hemopexin | NP_000604.1, NM_000613.2 | 2, 5 |
| | A2M | alpha-2-macroglobulin | NP_000005.2, NM_000014.4 | 3, 6 |

To obtain a biomarker signature, the protein level, protein activity level, mRNA level, etc. of the one or more biomarkers of interest is detected. That is, the representation of 1 or more, 2 or more, or 3 or more biomarkers, e.g. a panel of biomarkers, is determined. The biomarker level is typically measured by analyzing a body fluid sample (e.g., a sample of blood, e.g., whole blood, fractionated blood, plasma, serum, etc.) that is obtained from an individual. The sample that is collected may be freshly assayed or it may be stored and assayed at a later time. If the latter, the sample may be stored by any convenient means that will preserve the sample so that gene expression may be assayed at a later date. For example the sample may freshly cryopreserved, that is, cryopreserved without impregnation with fixative, e.g. at 4° C., at −20° C., at −60° C., at −80° C., or under liquid nitrogen. Alternatively, the sample may be fixed and preserved, e.g. at room temperature, at 4° C., at −20° C., at −60° C., at −80° C., or under liquid nitrogen, using any of a number of fixatives known in the art, e.g. alcohol, methanol, acetone, formalin, paraformaldehyde, etc.

The sample may be assayed as a whole sample, e.g. in crude form. Alternatively, the sample may be fractionated prior to analysis, e.g. for a blood sample, to purify leukocytes if, e.g., the biomarker to be assayed is an intracellular protein, or an RNA, to purify plasma or serum if, e.g., the biomarker is a secreted polypeptide. Further fractionation may also be performed, e.g., for a purified leukocyte sample, fractionation by e.g. panning, magnetic bead sorting, or fluorescence activated cell sorting (FACS) may be performed to enrich for particular types of cells, thereby arriving at an enriched population of that cell type for analysis; or, e.g., for a plasma or serum sample, fractionation based upon size, charge, mass, or other physical characteristic may be performed to purify particular secreted polypeptides, e.g. under denaturing or non-denaturing ("native") conditions, depending on whether or not a non-denatured form is required for detection. One or more fractions are then assayed to measure the expression levels of the one or more genes of interest. As such, the term "blood" as used herein is inclusive of whole blood as well as any fractionated portion thereof (e.g., blood cell fractions, plasma, serum, etc.).

The representation of the one or more biomarkers of interest may be measured by any convenient method known in the art for measuring protein levels, protein activity levels, polynucleotide, i.e. mRNA, levels, etc.

Figure 12:
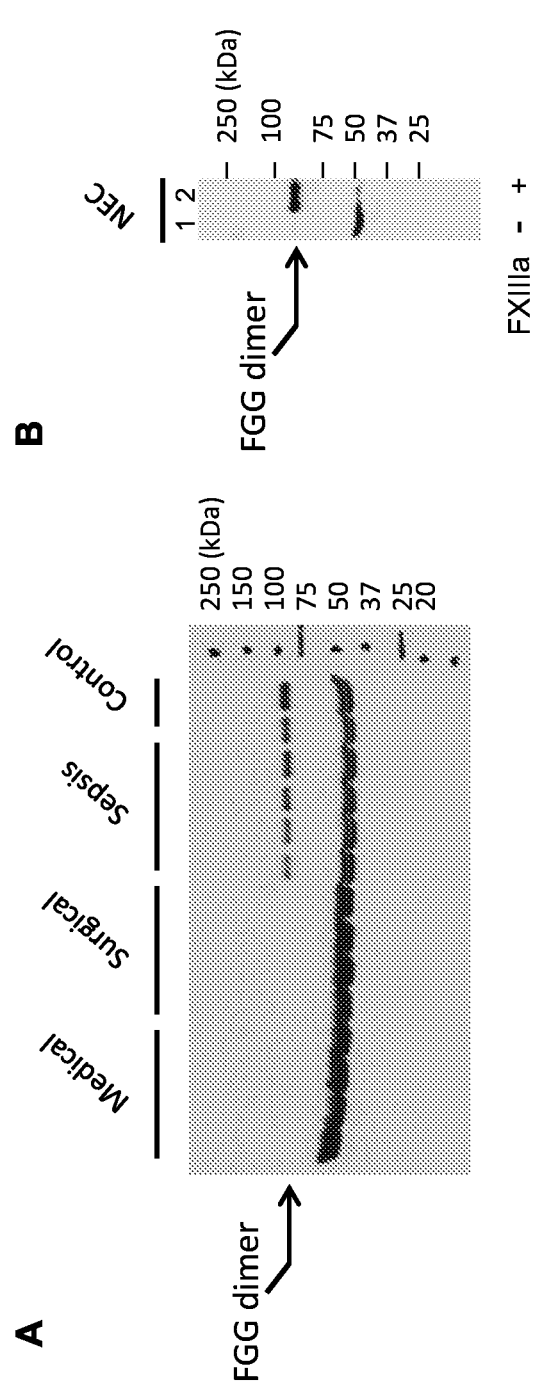
FIG. 12 demonstrates that FGG dimers are significantly decreased in NEC plasma samples as compared to sepsis or control samples, and that the formation of FGG-dimers can be induced by the addition of FXIIIa to pooled NEC samples. This figure depicts the validation of FGG dimers as an NEC-Dx biomarker.

For example, the representation of the subject FGG dimer biomarker in a sample may be detected by SDS-PAGE (sodium dodecyl sulfate polyacrylamide gel electrophoresis), followed by Western blotting with an anti-FGG antibody (e.g., see FIG. 12). Any convenient anti-FGG antibody can be used for the detection of FGG dimers (e.g., antibody 2G10-1, a mouse monoclonal antibody that reacts with FGG amino acids 15-35; anti-FGG rabbit polyclonal antibodies; and the like). As would be readily appreciated by one of ordinary skill in the art, because an FGG dimer has an increased molecular weight compared to an FGG monomer, the dimer runs slower on an SDS-PAGE gel, and the dimer band is therefore higher (i.e., above) than the monomer band. Additionally, because the FGG dimer is formed by a covalent bond (via the transglutaminase activity of FXIII), an FGG dimer can be distinguished from an FGG monomer using any convenient method (e.g., SDS-PAGE, size-exclusion chromatography, and the like) that can distinguish proteins based on molecular weight (i.e., size). Additionally, non-antibody-based methods of FGG dimer detection can be used. As one non-limiting example, fibrinogen can be mixed with thrombin in the appropriate buffer conditions, and further mixed with FXIII (from a patient), and the resulting fibrinogen reaction products can be examined, for example, by SDS-PAGE and staining with Coomassie brilliant blue.

For non-limiting examples of detecting FGG dimer, see (i) Kani et al, Blood. 2006 Sep. 15; 108(6):1887-94: "Analysis of fibrinogen variants at gamma387Ile shows that the side chain of gamma387 and the tertiary structure of the gammaC-terminal tail are important not only for assembly and secretion of fibrinogen but also for lateral aggregation of protofibrils and XIIIa-catalyzed gamma-gamma dimer formation"; (ii) Gerner et al, Thromb Haemost. 2001 March; 85(3):494-501: "Elevated plasma levels of crosslinked fibrinogen gamma-chain dimer indicate cancer-related fibrin deposition and fibrinolysis"; and (iii) Weerasinghe et al, Hepatology. 2011 April; 53(4):1323-32: "Fibrinogen-γ proteolysis and solubility dynamics during apoptotic mouse liver injury: heparin prevents and treats liver damage"; the disclosures of which are herein incorporated by reference for their teachings about FGG dimer detection.

As another example, the representation of the subject Factor XIII biomarker in a sample may be measured by detecting the amount of FXIII polypeptide by ELISA (enzyme-linked immunosorbent assay) method (e.g., see FIG. 13), e.g. as described below. Additionally or alternatively, transglutaminase activity of FXIII can be measured. Because FGG dimerizes due to the transglutaminase activity of FXIII, transglutaminase activity of FXIII can be measured by monitoring FGG dimer formation (see FIG. 14, where thrombin was added to activate FXIII and FGG dimer formation was monitored). FXIII transglutaminase activity can also be measured by any convenient method, which will be known to one of ordinary skill in the art. For example, a convenient colorimetric assay can be used to measure FXIII transglutaminase activity (Hitomi et al, Anal Biochem. 2009 Nov. 15; 394(2):281-3: "A specific colorimetric assay for measuring transglutaminase 1 and factor XIII activities"; which reference is hereby incorporated by reference in its entirety).

As another example, the amount or level in the sample of one or more proteins/polypeptides encoded by a gene of interest is determined. Any convenient protocol for evaluating protein levels may be employed where the level of one or more proteins in the assayed sample is determined. For antibody-based methods of protein level determination, any convenient antibody can be used that specifically binds to the intended biomarker (e.g., A2M, AGT, HPX, FXIII, FGG). The terms "specifically binds" or "specific binding" as used herein refer to preferential binding to a molecule relative to other molecules or moieties in a solution or reaction mixture (e.g., an antibody specifically binds to a particular polypeptide or epitope relative to other available polypeptides or epitopes). In some embodiments, the affinity of one molecule for another molecule to which it specifically binds is characterized by a KD (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). By "Affinity" it is meant the strength of binding, increased binding affinity being correlated with a lower KD.

While a variety of different manners of assaying for protein levels are known in the art, one representative and convenient type of protocol for assaying protein levels is ELISA. In ELISA and ELISA-based assays, one or more antibodies specific for the proteins of interest may be immobilized onto a selected solid surface, preferably a surface exhibiting a protein affinity such as the wells of a polystyrene microtiter plate. After washing to remove incompletely adsorbed material, the assay plate wells are coated with a non-specific "blocking" protein that is known to be antigenically neutral with regard to the test sample such as bovine serum albumin (BSA), casein or solutions of powdered milk. This allows for blocking of non-specific adsorption sites on the immobilizing surface, thereby reducing the background caused by non-specific binding of antigen onto the surface. After washing to remove unbound blocking protein, the immobilizing surface is contacted with the sample to be tested under conditions that are conducive to immune complex (antigen/antibody) formation. Such conditions include diluting the sample with diluents such as BSA or bovine gamma globulin (BGG) in phosphate buffered saline (PBS)/Tween or PBS/Triton-X 100, which also tend to assist in the reduction of nonspecific background, and allowing the sample to incubate for about 2-4 hrs at temperatures on the order of about 25°-27° C. (although other temperatures may be used). Following incubation, the antisera-contacted surface is washed so as to remove non-immunocomplexed material. An exemplary washing procedure includes washing with a solution such as PBS/Tween, PBS/Triton-X 100, or borate buffer. The occurrence and amount of immunocomplex formation may then be determined by subjecting the bound immunocomplexes to a second antibody having specificity for the target that differs from the first antibody and detecting binding of the second antibody. In certain embodiments, the second antibody will have an associated enzyme, e.g. urease, peroxidase, or alkaline phosphatase, which will generate a color precipitate upon incubating with an appropriate chromogenic substrate. For example, a urease or peroxidase-conjugated anti-human IgG may be employed, for a period of time and under conditions which favor the development of immunocomplex formation (e.g., incubation for 2 hr at room temperature in a PBS-containing solution such as PBS/Tween). After such incubation with the second antibody and washing to remove unbound material, the amount of label is quantified, for example by incubation with a chromogenic substrate such as urea and bromocresol purple in the case of a urease label or 2,2'-azino-di-(3-ethyl-benzthiazoline)-6-sulfonic acid (ABTS) and H2O2, in the case of a peroxidase label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The solid substrate upon which the antibody or antibodies are immobilized can be made of a wide variety of materials and in a wide variety of shapes, e.g., microtiter plate, microbead, dipstick, resin particle, etc. The substrate may be chosen to maximize signal to noise ratios, to minimize background binding, as well as for ease of separation and cost. Washes may be effected in a manner most appropriate for the substrate being used, for example, by removing a bead or dipstick from a reservoir, emptying or diluting a reservoir such as a microtiter plate well, or rinsing a bead, particle, chromatograpic column or filter with a wash solution or solvent.

Alternatively, non-ELISA based-methods for measuring the levels of one or more proteins in a sample may be employed and any convenient method may be used. Representative examples known to one of ordinary skill in the art include but are not limited to mass spectrometry, proteomic arrays, xMAP™ microsphere technology, western blotting, immunohistochemistry, flow cytometry, and detection in body fluid by electrochemical sensor. In, for example, flow cytometry methods, the quantitative level of gene products of the one or more genes of interest are detected on cells in a cell suspension by lasers. As with ELISAs and immunohistochemistry, antibodies (e.g., monoclonal antibodies) that specifically bind the polypeptides encoded by the genes of interest are used in such methods. As another example, electrochemical sensors may be employed. In such methods, a capture aptamer or an antibody that is specific for a target protein (the "analyte") is immobilized on an electrode. A second aptamer or antibody, also specific for the target protein, is labeled with, for example, pyrroquinoline quinone glucose dehydrogenase ((PQQ)GDH). The sample of body fluid is introduced to the sensor either by submerging the electrodes in body fluid or by adding the sample fluid to a sample chamber, and the analyte allowed to interact with the labeled aptamer/antibody and the immobilized capture aptamer/antibody. Glucose is then provided to the sample, and the electric current generated by (PQQ)GDH is observed, where the amount of electric current passing through the electrochemical cell is directly related to the amount of analyte captured at the electrode.

For measuring protein activity levels, the amount or level of protein activity in the sample of one or more proteins/polypeptides encoded by the gene of interest is determined.

As another example, the amount or level in the sample of one or more RNAs encoded by a gene of interest is determined. Any convenient method for measuring mRNA levels in a sample may be used, e.g. hybridization-based methods, e.g. northern blotting and in situ hybridization (Parker & Barnes, Methods in Molecular Biology 106:247-283 (1999)), RNAse protection assays (Hod, Biotechniques 13:852-854 (1992)), and PCR-based methods (e.g. reverse transcription PCR (RT-PCR) (Weis et al., Trends in Genetics 8:263-264 (1992)). Alternatively, any convenient method for measuring protein levels in a sample may be used, e.g. antibody-based methods, e.g. immunoassays, e.g., enzyme-linked immunosorbent assays (ELISAs), immunohistochemistry, and flow cytometry (FACS).

For measuring mRNA levels, the starting material may betotal RNA, i.e. unfractionated RNA, or poly A+ RNA isolated from a suspension of cells, e.g. a peripheral blood sample. General methods for mRNA extraction are well known in the art and are disclosed in standard textbooks of molecular biology, including Ausubel et al., Current Protocols of Molecular Biology, John Wiley and Sons (1997).

RNA isolation can also be performed using a purification kit, buffer set and protease from commercial manufacturers, according to the manufacturer's instructions. For example, RNA from cell suspensions can be isolated using Qiagen RNeasy mini-columns, and RNA from cell suspensions or homogenized tissue samples can be isolated using the TRIzol reagent-based kits (Invitrogen), MasterPure™ Complete DNA and RNA Purification Kit (EPICENTRE™, Madison, Wis.), Paraffin Block RNA Isolation Kit (Ambion, Inc.) or RNA Stat-60 kit (Tel-Test).

mRNA levels may be measured by any convenient method. Examples of methods for measuring mRNA levels may be found in, e.g., the field of differential gene expression analysis. One representative and convenient type of protocol for measuring mRNA levels is array-based gene expression profiling. Such protocols are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Specific hybridization technology which may be practiced to generate the expression signatures employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions, and unbound nucleic acid is then removed. The term "stringent assay conditions" as used herein refers to conditions that are compatible to produce binding pairs of nucleic acids, e.g., surface bound and solution phase nucleic acids, of sufficient complementarity to provide for the desired level of specificity in the assay while being less compatible to the formation of binding pairs between binding members of insufficient complementarity to provide for the desired specificity. Stringent assay conditions are the summation or combination (totality) of both hybridization and wash conditions.

The resultant pattern of hybridized nucleic acid provides information regarding expression for each of the genes that have been probed, where the expression information is in terms of whether or not the gene is expressed and, typically, at what level, where the expression data, i.e., expression profile (e.g., in the form of a transcriptosome), may be both qualitative and quantitative.

Additionally or alternatively, non-array based methods for quantitating the level of one or more nucleic acids in a sample may be employed. These include those based on amplification protocols, e.g., Polymerase Chain Reaction (PCR)-based assays, including quantitative PCR, reverse-transcription PCR (RT-PCR), real-time PCR, and the like, e.g. TaqMan® RT-PCR, MassARRAY® System, BeadArray® technology, and Luminex technology; and those that rely upon hybridization of probes to filters, e.g. Northern blotting and in situ hybridization.

The resultant data provides information regarding expression and/or activity for each of the biomarkers that have been measured, wherein the information is in terms of whether or not the biomarker is present (e.g. expressed and/or active) and, typically, at what level, and wherein the data may be both qualitative and quantitative.

Once the representation of the one or more biomarkers has been determined, the measurement(s) may be analyzed in any of a number of ways to obtain a biomarker signature.

For example, the representation of the one or more biomarkers may be analyzed individually to develop a NEC biomarker profile. As used herein, a "biomarker profile" is the normalized representation of one or more biomarkers in a patient sample, for example, the normalized level of serological protein concentrations in a patient sample, the normalized activity of a biomarker in the sample, etc. A profile may be generated by any of a number of methods known in the art. For example, the level of each marker may be $\log_2$ transformed and normalized relative to the expression of a selected housekeeping gene, e.g. ABL1, GAPDH, or PGK1, or relative to the signal across a whole panel, etc. Other methods of calculating a biomarker signature will be readily known to the ordinarily skilled artisan. In certain embodiments, the biomarker profile may be a "protein biomarker profile", or simply "protein profile", i.e. it comprises the normalized expression level(s) of the one or more biomarkers in a patient sample as determined by measuring the amount of amino acid product encoded by the biomarker(s). In certain embodiments, the biomarker profile may be a "protein activity biomarker profile", or simply "protein activity profile", i.e. it comprises the normalized activity of the one or more biomarkers in a patient sample as determined by measuring the amount of activity exhibited in the sample. In certain embodiments, the biomarker profile may be a "RNA biomarker profile", or simply "RNA profile", i.e. it comprises the normalized expression level of the one or more biomarkers in a patient sample as determined by measuring the amount of RNA transcribed from the one or more biomarkers.

As another example, the measurements of a panel of biomarkers may be analyzed collectively to arrive at a single NEC biomarker score, and the NEC biomarker signature is therefore a single score. By "biomarker score" it is meant a single metric value that represents the sum of the weighted representations of each of the biomarkers of interest, more usually two or more biomarkers of interest, in a biomarker panel (e.g., a NEC-Dx biomarker panel, NEC-S-Dx biomarker panel, etc.). As such, in some embodiments, the subject method comprises detecting the amount/activity of markers of an NEC biomarker panel in the sample, and calculating an NEC biomarker score based on the weighted levels of the biomarkers. In certain embodiments, the biomarker score may be a "protein biomarker score", or simply "protein score", i.e. it comprises the weighted expression level(s) of the one or more biomarkers, e.g. each biomarker in a panel of biomarkers, in a patient sample as determined by measuring the amount of amino acid product encoded by the biomarker(s). In certain embodiments, the biomarker score may be a "protein activity biomarker score", or simply "protein activity score", i.e. it comprises the weighted activity of the one or more biomarkers, e.g. each biomarker in a panel of biomarkers, in a patient sample as determined by measuring the amount of activity exhibited in the sample. In certain embodiments, the biomarker score may be a "RNA biomarker score", or simply "RNA score", i.e. it comprises the weighted expression level of the one or more biomarkers, e.g. each biomarker in a panel of biomarkers, in a patient sample as determined by measuring the amount of RNA transcribed from the one or more biomarkers.

An NEC biomarker score for a patient sample (e.g., an NEC-Dx biomarker score, and NEC-S-Dx biomarker score, etc.) may be calculated by any of a number of methods and algorithms known in the art for calculating biomarker scores. For example, weighted marker levels, e.g. $log_2$ transformed and normalized marker levels that have been weighted by, e.g., multiplying each normalized marker level to a weighting factor, may be totaled and in some cases averaged to arrive at a single value representative of the panel of biomarkers analyzed.

In some instances, the weighting factor, or simply "weight" for each marker in a panel may be a reflection of the change in analyte level in the sample. For example, the analyte level of each biomarker may be $log_2$ transformed and weighted either as 1 (for those markers that are increased in level in NEC, or NEC-S, etc.) or −1 (for those markers that are decreased in level in NEC, or NEC-S, etc.), and the ratio between the sum of increased markers as compared to decreased markers determined to arrive at an NEC biomarker signature. In other instances, the weights may be reflective of the importance of each marker to the specificity, sensitivity and/or accuracy of the marker panel in making the diagnostic, prognostic, or monitoring assessment. Such weights may be determined by any convenient statistical machine learning methodology, e.g. Principle Component Analysis (PCA), linear regression, support vector machines (SVMs), and/or random forests of the dataset from which the sample was obtained may be used. In some instances, weights for each marker are defined by the dataset from which the patient sample was obtained. In other instances, weights for each marker may be defined based on a reference dataset, or "training dataset". Methods of analysis may be readily performed by one of ordinary skill in the art by employing a computer-based system, e.g. using any hardware, software and data storage medium as is known in the art, and employing any algorithms convenient for such analysis. For example, data mining algorithms can be applied through "cloud computing", smartphone based or client-server based platforms, and the like.

Thus, in some instances, an NEC biomarker signature may be expressed as more than one value (e.g., as a biomarker profile, i.e. the normalized expression values for multiple biomarkers), while in other instances, the NEC biomarker signature may be expressed as a single value (e.g., an NEC biomarker score).

In some cases, two NEC biomarker signatures may be obtained. For example, an NEC-Dx biomarker signature and an NEC-S-Dx biomarker signature may be obtained. In some cases, an NEC clinical score can be integrated into an NEC biomarker signature (and/or an NEC biomarker score) such that an NEC biomarker signature (or NEC biomarker score) represents NEC biomarker data combined with NEC clinical data. Details on clinical assessments that may be and clinical scores that may be used in these embodiments are well known in the art and are described in greater detail below.

In certain embodiments the expression, e.g. polypeptide level, of only one marker is evaluated to produce a biomarker signature. In yet other embodiments, the levels of two or more, i.e. a panel, markers, e.g., 3 or more, 4 or more, 5 or more, 6 or more, 7 or more, 8 or more, 10 or more, or 15 or more markers is evaluated. Accordingly, in the subject methods, the expression of at least one marker in a sample is evaluated. In certain embodiments, the evaluation that is made may be viewed as an evaluation of the proteome, as that term is employed in the art.

In some instances, the subject methods of determining or obtaining a NEC biomarker signature (e.g. NEC biomarker profile or NEC biomarker score) for a subject further comprise providing the NEC biomarker signature as a report. Thus, in some instances, the subject methods may further include a step of generating or outputting a report providing the results of a NEC biomarker evaluation in the sample, which report can be provided in the form of an electronic medium (e.g., an electronic display on a computer monitor), or in the form of a tangible medium (e.g., a report printed on paper or other tangible medium). Any form of report may be provided, e.g. as known in the art or as described in greater detail below.

Employing an NEC Biomarker Signature to Evaluate a Subject.

The NEC biomarker signature (e.g., an NEC-S-Dx biomarker signature and/or an NEC-Dx biomarker signature) that is so obtained may be employed to make an NEC assessment, e.g. to diagnose NEC, to provide a prognosis to a patient at risk for developing NEC, to provide a prediction of the responsiveness of a patient with NEC to a medical therapy, to provide a prediction of whether a patient requires surgery to prevent mortality from NEC (e.g. to diagnose NEC-S), to treat a patient having NEC, etc. In some instances, the patient is suspected of having NEC or sepsis. A patient that is suspected of having NEC or sepsis is one in which historical factors, physical findings and radiological findings that indicate risk for NEC or sepsis. Historical factors include, for example, feeding intolerance (defined as vomiting two or more feedings within 24 hours or any vomit containing bile, or the presence of gastric residuals of volume greater than 6 cc/kg or any aspirate containing bile), apneic/bradycardic episodes, oxygen desaturation episodes, guaiac positive, or bloody stools. Physical findings include, for example, abdominal distention, capillary refill time>2 sec, abdominal wall discoloration, or abdominal tenderness. Radiological findings include, for example, pneumatosis intestinalis, portal venous gas, Ileus, dilated bowel, pneumoperitoneum, air/fluid levels, thickened bowel walls, ascites or peritoneal fluid, or free intraperitoneal air, absent bowel sounds, hypotension, abdominal cellulitis, and right lower quadrant mass. In other instances, the patient is not suspected of having NEC or sepsis, e.g. the patient may have no clinical symptoms or risk factors for NEC or sepsis.

Typically, in making an NEC assessment, the biomarker signature that is obtained is employed by comparing it to a reference or control, and using the results of that comparison (a "comparison result") to determine a diagnosis, prognosis or prediction. The terms "reference" or "control", e.g. "reference signature" or "control signature", "reference profile" or "control profile", and "reference score" or "control score' as used herein mean a standardized biomarker signature, e.g. biomarker profile or biomarker score, that may be used to interpret the NEC biomarker signature of a given patient and assign a diagnostic, prognostic, and/or responsiveness class thereto. The reference or control is typically a biomarker signature that is obtained from a sample (e.g., a body fluid or a tissue) with a known association with a particular phenotype (e.g., NEC, NEC-S, NEC-M, sepsis, control (no NEC), etc). Thus, in some embodiments, the reference sample is a NEC reference sample (i.e., a sample from a person (or from multiple people) known to have NEC). In some embodiments, the reference sample is a NEC-S reference sample (i.e., a sample from a person (or from multiple people) known to have NEC-S). In some embodiments, the reference sample is a NEC-M reference sample (i.e., a sample from a person (or from multiple people) known to have NEC-M). In some embodiments, the reference sample is a sepsis reference sample (i.e., a sample from a person (or from multiple people) known to have sepsis). In some embodiments, the reference sample is a non-NEC reference sample (i.e., a sample from a person (or from multiple people) known to not to have NEC). In some embodiments, the reference sample is a non-NEC-S reference sample (i.e., a sample from a person (or from multiple people) known not to have NEC-S). In some embodiments, the reference sample is a non-NEC-M reference sample (i.e., a sample from a person (or from multiple people) known not to have NEC-M). In some embodiments, the reference sample is a non-sepsis reference sample (i.e., a sample from a person (or from multiple people) known not to have sepsis).

For example, high-risk phenotypes, e.g. increased or decreased expression of particular panels of genes, are associated with samples from certain patient cohorts, i.e. positive controls, e.g. increased or decreased expression of NEC-S-Dx biomarkers is associated with samples from NEC-S patients. Thus, a positive control reference that may be used when making an NEC-S diagnosis could be a NEC-S-Dx biomarker signature (e.g., an NEC-S-Dx profile or NEC-S-Dx score) of a body fluid sample from a patient with NEC-S; As another example, low-risk phenotypes e.g. normal expression of particular panels of genes, are associated with sample from unaffected patients, i.e., negative controls. Thus, the negative control reference when making an NEC-S diagnosis may be a NEC-S-Dx signature (e.g., an NEC-S-Sx profile or NEC-S-Dx score) of a body fluid sample from an individual that is not affected with NEC-S, e.g. a healthy individual, an individual with sepsis, or and individual with NEC-M.

For example, an increased level of AGT and/or a decreased level of A2M and/or a decreased level of HPX in an NEC-S-Dx biomarker signature from a patient relative to the respective levels in a negative control reference (i.e., an NEC-S-Dx signature of a body fluid sample from an individual that is not affected with NEC-S, an NEC-S-Dx signature of a body fluid sample from an individual that is healthy, an NEC-S-Dx signature of a body fluid sample from an individual that is affected with NEC but will likely respond to medical treatment, an NEC-S-Dx signature of a body fluid sample from an individual that has sepsis, etc.) is indicative of a positive diagnosis of NEC-S in the patient (i.e., the patient is at high risk of being an NEC-S patient). Likewise, a level of AGT and/or A2M and/or HPX in an NEC-S-Dx biomarker signature from a patient that is substantially similar to the level of AG and/or A2M and/or HPX, respectively, in a positive control reference (i.e., an NEC-S-Dx signature of a body fluid sample from an individual that is affected with NEC-S) is indicative of a positive diagnosis of NEC-S in the patient (i.e., the patient is at high risk of being an NEC-S patient).

As another example, a level of AGT and/or A2M and/or HPX in an NEC-S-Dx biomarker signature from a patient that is substantially similar to the level of AGT and/or A2M and/or HPX, respectively, in a negative control reference (i.e., an NEC-S-Dx signature of a body fluid sample from an individual that is not affected with NEC-S, an NEC-S-Dx signature of a body fluid sample from an individual that is healthy, an NEC-S-Dx signature of a body fluid sample from an individual that is affected with NEC but will likely respond to medical treatment, an NEC-S-Dx signature of a body fluid sample from an individual that has sepsis, etc.) is indicative of a negative diagnosis of NEC-S in the patient (i.e., the patient is at low risk of being an NEC-S patient). Likewise, a decreased level of AGT and/or an increased level of A2M and/or an increased level of HPX in an NEC-S-Dx biomarker signature from a patient relative to the respective levels in a positive control reference (i.e., an NEC-S-Dx signature of a body fluid sample from an individual that is affected with NEC-S) is indicative of a negative diagnosis of NEC-S in the patient (i.e., the patient is at low risk of being a NEC-S patient).

In certain embodiments, the obtained biomarker signature for a subject is compared to a single reference/control biomarker signature to obtain information regarding the phenotype. In yet other embodiments, the obtained biomarker signature for the subject is compared to two or more different reference/control biomarker signatures to obtain more in-depth information regarding the phenotype of the assayed tissue. For example, an biomarker profile may be compared to both a positive biomarker profile and a negative biomarker profile, or an biomarker score may be compared to both a positive biomarker score and a negative biomarker score to obtain confirmed information regarding whether the tissue has the phenotype of interest. As another example, a biomarker profile or score may be compared to multiple biomarker profiles or scores, each correlating with a particular diagnosis, prognosis or therapeutic responsiveness.

As discussed above, an NEC biomarker signature may be employed to make an NEC assessment. For example, a patient can be diagnosed as having NEC depending on whether his NEC-Dx biomarker signature correlates more closely with the NEC-Dx signature of one or more patients with NEC, e.g. the median across a cohort of patients with NEC, or whether his signature correlates more closely with the median NEC-Dx signature across a cohort of individuals without NEC. As another example, a patient can be diagnosed as being at high risk for having NEC-S or as being at low risk for having NEC-S depending on whether his NEC-S-Dx signature correlates more closely with the signature of a patient with NEC-S (or, e.g., with the median NEC-S-Dx signature across a cohort of patients with NEC-S), or whether his signature correlates more closely with the signature of a patient unaffected by NEC-S (or, e.g., with the median NEC-S-Dx signature across a cohort of individuals unaffected by NEC-S). By "correlates closely", it is meant is within about 40% of the reference signature, e.g. 40%, 35%, or 30%, in some embodiments within 25%, 20%, or 15%, sometimes within 10%, 8%, 5%, or less. Alternatively, when two or more references are used, e.g. both a reference from patient or cohort of patients with NEC and a reference from a patient or cohort of unaffected individuals, a patient can be diagnosed as being at high risk for having NEC-S or as being at low risk for having NEC-S depending on whether his signature correlates more closely with the median NEC-S-Dx signature of a patient or cohort of patients with NEC-S or an individual or cohort of individual unaffected by NEC-S.

As also discussed above, an NEC-S-Dx biomarker signature may be employed to provide a prognosis to a patient suspected of or diagnosed as having NEC. For example, a patient can be ascribed to high- or low-risk categories, or high-, medium- or low-risk categories for overall survival depending on whether their NEC-S-Dx signature correlates more closely with the median NEC-S-Dx signature across a cohort of patients with the M class of the disease or the S class of the disease patient, the overall survival rates of patients with M class NEC or S class NEC being known in the art or readily determined by the ordinarily skilled artisans by, e.g., Kaplan-Meier analysis of individuals with M-class NEC and S-class NEC.

As also discussed above, an NEC-S-Dx biomarker signature may be employed to provide a prediction of responsiveness of a patient to a particular therapy, e.g. medical therapy or surgery (which can be a diagnosis of NEC-S versus NEC-M and/or a prognosis of NEC-S for a patient with NEC). These predictive methods can be used to assist patients and physicians in making treatment decisions, e.g. in choosing the most appropriate treatment modalities for any particular patient.

Additionally, the NEC-S-Dx biomarker signature may be used on samples collected from patients in a clinical trial and the results of the test used in conjunction with patient outcomes in order to determine whether subgroups of patients are more or less likely to show a response to a new drug than the whole group or other subgroups. Further, such methods can be used to identify from clinical data the subsets of patients who can benefit from therapy. Additionally, a patient is more likely to be included in a clinical trial if the results of the test indicate a higher likelihood that the patient will be responsive to medical treatment, and a patient is less likely to be included in a clinical trial if the results of the test indicate a lower likelihood that the patient will be responsive to medical treatment.

The subject methods can be used alone or in combination with other clinical methods for patient stratification known in the art to provide a diagnosis, a prognosis, or a prediction of responsiveness to therapy. For example, clinical parameters that are known in the art for diagnosing NEC, diagnosing types of NEC, or staging NEC, or for diagnosing or staging sepsis, may also be incorporated into the ordinarily skilled artisan's analysis to arrive at a diagnosis, prognosis, or prediction of responsiveness to therapy with the subject methods.

For example, one common clinically used set of criteria for staging Necrotizing Enterocolitis is Modified Bell's criteria, described in detail in Table 2 below. In some embodiments, an NEC clinical score may be obtained, that NEC clinical score comprising data on the clinical findings regarding the patient, for example on the pH value of blood; portal venous gas in x-ray; abdominal ileus in x-ray; the use of a vasopressor prior to diagnosis; abdominal distention; whether cranial ultrasound was done for ivh (intra-ventricular hemorrhage); vasopressor on diagnosis, i.e. the patient is receiving medications that support blood pressure, e.g. inotropes, chronotropes, alpha agonists and the like, e.g. dopamine; ventilation on diagnosis; whether any positive culture of bacteria or fungus was obtained from blood or urine within 5 days of diagnosis; the gestational age of the patient at birth; (and the patient's birth weight. The NEC clinical score is then used in conjunction with the biomarker signature (or, e.g., an NEC-Dx biomarker signature) to provide a diagnosis (e.g., an NEC diagnosis, an NEC-S diagnosis, and the like) with greater accuracy, specificity and sensitivity. For example, the NEC-S-Dx signature (and/or an NEC-Dx biomarker signature) and the NEC clinical score are compared to an NEC-S-Dx signature (and/or an NEC-Dx biomarker signature) and an NEC clinical score from a reference sample, and the results of both comparisons are employed to provide a diagnosis (e.g., an NEC diagnosis, an NEC-S diagnosis, and the like) to the patient; In some embodiments, the NEC clinical score is used alongside the biomarker signature (and/or biomarker signature) of the subject methods. In other embodiments, the NEC clinical score is integrated with the expression score to obtain a single metric value that is representative of both the NEC clinical score and the expression score, i.e. an NEC-S-gene/clinic score (an "NEC-G/C score"), e.g. an NEC-S-Dx G/C score, where that integrated score is compared to an integrated score for a reference sample, at the results of this comparison are employed to provide a prognosis to the patient or to predict the responsiveness of the patient to medical therapy.

TABLE 2

Modified Bell's criteria for staging Necrotizing Enterocolitis. "NPO" = nothing by mouth

| Stage | Systemic signs | Abdominal signs | Radiographic signs | Treatment |
|---|---|---|---|---|
| IA Suspected | Temperature instability, apnea, bradycardia, lethargy | Gastric retention, abdominal distention, emesis, heme-positive stool | Normal or intestinal dilation, mild ileus | NPO, antibiotics × 3 days |
| IB Suspected | Same as above | Grossly bloody stool | Same as above | Same as IA |
| IIA Definite, mildly ill | Same as above | Same as above, plus absent bowel sounds with or without abdominal tenderness | Intestinal dilation, ileus, pneumatosis intestinalis | NPO, antibiotics × 7 to 10 days |
| IIB Definite, moderately ill | Same as above, plus mild metabolic acidosis and thrombocytopenia | Same as above, plus absent bowel sounds, definite tenderness, with or without abdominal cellulitis or right lower quadrant mass | Same as IIA, plus ascites | NPO, antibiotics × 14 days |

TABLE 2-continued

Modified Bell's criteria for staging Necrotizing Enterocolitis.
"NPO" = nothing by mouth

| Stage | Systemic signs | Abdominal signs | Radiographic signs | Treatment |
|---|---|---|---|---|
| IIIA Advanced, severely ill, intact bowel | Same as IIB, plus hypotension, bradycardia, severe apnea, combined respiratory and metabolic acidosis, Disseminated Intravascular Coagulation (DIC), and neutropenia | Same as above, plus signs of peritonitis, marked tenderness, and abdominal distention | Same as IIA, plus ascites | NPO, antibiotics × 14 days, fluid resuscitation, inotropic support, ventilator therapy, paracentesis |
| IIIB Advanced, severely ill, perforated bowel | Same as IIIA | Same as IIIA | Same as above, plus pneumo-peritoneum | Same as IIA, plus surgery |

As another example, the American College of Chest Physicians and the Society of Critical Care Medicine describes several different levels of sepsis (see Table 3, below). In some embodiments, a sepsis clinical score may be obtained, that sepsis clinical score comprising data on the clinical findings regarding the patient as described in the table.

In some embodiments, a sepsis clinical score is used alongside the biomarker signature of the subject methods. In other embodiments, the sepsis clinical score is integrated with the expression score to obtain a single metric value that is representative of both the sepsis clinical score and the expression score and the results of this comparison are employed to provide a prognosis to the patient or to predict the responsiveness of the patient to medical therapy.

TABLE 3

Sepsis levels, as described by the American College of Chest Physicians
and the Society of Critical Care Medicine \* Systemic inflammatory response syndrome (SIRS).

Defined by the presence of two or more of the following findings:
Body temperature <36° C. (97° F.) or >38° C. (100° F.)
(hypothermia or fever).
Heart rate >90 beats per minute.
Respiratory rate >20 breaths per minute or, on blood gas, a PaCO2 less
than 32 mm Hg (4.3 kPa) (tachypnea or hypocapnia due to
hyperventilation). White blood cell count <4,000 cells/mm3 or >12,000
cells/mm3 (<4 × 109 or >12 × 109 cells/L), or greater than 10% band
forms
(immature white blood cells). (leukopenia, leukocytosis, or bandemia).

\* Sepsis.

Defined as SIRS in response to a confirmed infectious process. Infection
can be suspected or proven (by culture, stain, or polymerase chain reaction
(PCR)), or a clinical syndrome pathognomonic for infection. Specific
evidence for infection includes WBCs in normally sterile fluid (such as
urine or cerebrospinal fluid (CSF), evidence of a perforated viscus (free air
on abdominal x-ray or CT scan, signs of acute peritonitis), abnormal chest
x-ray (CXR) consistent with pneumonia (with focal opacification), or
petechiae, purpura, or purpura fulminans TABLE 3-continued Sepsis levels, as described by the American College of Chest Physicians
and the Society of Critical Care Medicine \* Severe sepsis.

Defined as sepsis with organ dysfunction, hypoperfusion, or hypotension.

\* Septic shock.

Defined as sepsis with refractory arterial hypotension or hypoperfusion
abnormalities in spite of adequate fluid resuscitation. Signs of systemic
hypoperfusion may be either end-organ dysfunction or serum lactate
greater
than 4 mmol/dL. Other signs include oliguria and altered mental status.
Patients are defined as having septic shock if they have sepsis plus
hypotension after aggressive fluid resuscitation (typically upwards of 6
liters or 40 ml/kg of crystalloid).

Reports

In some embodiments, providing (i.e., making) an NEC assessment of a subject with suspected or confirmed NEC and/or NEC-S, i.e., a diagnosis of NEC, a diagnosis of NEC-S, a prognosis for a patient with NEC, or a prediction of responsiveness of a patient with NEC to medical intervention (i.e., medical therapy) and/or surgery, includes generating a written report that includes the artisan's assessment of the subject's current state of health i.e. a "diagnosis assessment", of the subject's prognosis, i.e. a "prognosis assessment", and/or of possible treatment regimens, i.e. a "treatment assessment". Thus, a subject method may further include a step of generating or outputting a report providing the results of a diagnosis assessment, a prognosis assessment, or treatment assessment, which report can be provided in the form of an electronic medium (e.g., an electronic display on a computer monitor), or in the form of a tangible medium (e.g., a report printed on paper or other tangible medium).

A "report," as described herein, is an electronic or tangible document which includes report elements that provide information of interest relating to a diagnosis assessment, a prognosis assessment, and/or a treatment assessment and its results. A subject report can be completely or partially electronically generated. A subject report includes at least an NEC assessment, e.g., a diagnosis as to whether a subject has a high likelihood of having NEC and/or NEC-S; or a prognosis assessment, i.e. a prediction of the responsiveness of a patient to NEC medical intervention; and/or a suggested course of treatment to be followed. A subject report can further include one or more of: 1) information regarding the testing facility; 2) service provider information; 3) subject data; 4) sample data; 5) an assessment report, which can include various information including: a) test data, where test data can include i) the biomarker levels of one or more NEC biomarkers; and/or ii) the biomarker signatures for one or more NEC biomarkers.

The report may include information about the testing facility, which information is relevant to the hospital, clinic, or laboratory in which sample gathering and/or data generation was conducted. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

The report may include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

The report may include a subject data section, including subject medical history as well as administrative subject data (that is, data that are not essential to the diagnosis, prognosis, or treatment assessment) such as information to identify the subject (e.g., name, subject date of birth (DOB), gender, mailing and/or residence address, medical record number (MRN), room and/or bed number in a healthcare facility), insurance information, and the like), the name of the subject's physician or other health professional who ordered the susceptibility prediction and, if different from the ordering physician, the name of a staff physician who is responsible for the subject's care (e.g., primary care physician).

The report may include a sample data section, which may provide information about the biological sample analyzed, such as the source of biological sample obtained from the subject (e.g. blood, e.g., whole blood, fractionated blood, plasma, serum, etc.)), how the sample was handled (e.g. storage temperature, preparatory protocols) and the date and time collected. Report fields with this information can generally be populated using data entered by the user, some of which may be provided as pre-scripted selections (e.g., using a drop-down menu).

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting. When in electronic format, the report is recorded on a suitable physical medium, such as a computer readable medium, e.g., in a computer memory, zip drive, CD, DVD, flash drive, etc.

It will be readily appreciated that the report can include all or some of the elements above, with the proviso that the report generally includes at least the elements sufficient to provide the analysis requested by the user (e.g., a diagnosis, a prognosis, or a prediction of responsiveness to a therapy).

Reagents, Devices and Kits

Also provided are reagents, devices and kits thereof for practicing one or more of the above-described methods. The subject reagents, devices and kits thereof may vary greatly. Reagents and devices of interest include those mentioned above with respect to the methods of assaying gene expression levels, where such reagents may include protein or RNA purification reagents, reagents for measuring protein activity, antibodies to NEC biomarker polypeptides (e.g., immobilized on a substrate, e.g., in the form of a dipstick, i.e., lateral flow assay device), nucleic acid primers specific for NEC biomarkers, arrays of nucleic acid probes, signal producing system reagents, etc., depending on the particular detection protocol to be performed. For example, reagents may include antibodies that are specific for one or more of the biomarkers AGT, A2M, HPX, FXIII and FGG (note: an antibody for FGG can be used to detect FGG dimer levels as well as FXIII protein activity levels). Other examples of reagents include arrays that comprise probes that are specific for one or more of the NEC biomarkers; antibodies to epitopes of the NEC biomarker proteins; or other reagents that may be used to detect the level of NEC biomarkers (e.g., FXIII transglutaminase colorimetric assay reagents for use in measuring the level of FXIII protein activity).

The subject kits may also comprise one or more biomarker signature references, e.g. a reference for an NEC-S-Dx signature (and/or a reference for an NEC biomarker signature), for use in employing the biomarker signature obtained from a patient sample. For example, the reference may be a sample of a known phenotype, e.g. an unaffected individual, or an affected individual, e.g. from a particular risk group that can be assayed alongside the patient sample, or the reference may be a report of disease diagnosis, disease prognosis, or responsiveness to therapy that is known to correlate with one or more of the subject NEC biomarker signatures.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A neonate is evaluated in the Neonatal Intensive Care Unit (NICU) with symptoms of NEC including temperature instability, apnea, metabolic acidosis, gastric retention, and abdominal distention. The doctor draws a blood sample from the patient and tests for the levels of AGT, A2M, and HPX proteins. The results of the test indicate AGT levels that are higher than AGT levels in individuals without NEC-S; and A2M and HPX levels that are lower than A2M and HPX levels in individuals without NEC-S. From this, the doctor provides a diagnosis of NEC-S and determines that the neonate requires surgery for treatment. The neonate is expected to recover from NEC.

Example 2

A neonate is evaluated in the Neonatal Intensive Care Unit (NICU) with symptoms of NEC. The doctor draws a blood sample from the patient and tests for the levels of AGT, A2M, and HPX proteins. The results of the test indicate AGT, A2M and HPX levels that are substantially similar to AGT, A2M and HPX levels in healthy individuals. From this, the doctor provides a negative diagnosis of NEC-S and prescribes a therapy of antibiotics and nothing by mouth to the neonate. The neonate is expected to recover from NEC.

Example 3

Samples from control patients and from patients with NEC-S, NEC-M, and sepsis were isolated and tested for levels of various proteins. FIGS. 3-9 illustrate that the levels of Alpha-2-macroglobulin (A2M), Hemopexin (HPX), and Angiotensinogen (AGT) correlate with patient subgroups.

Figure 3:
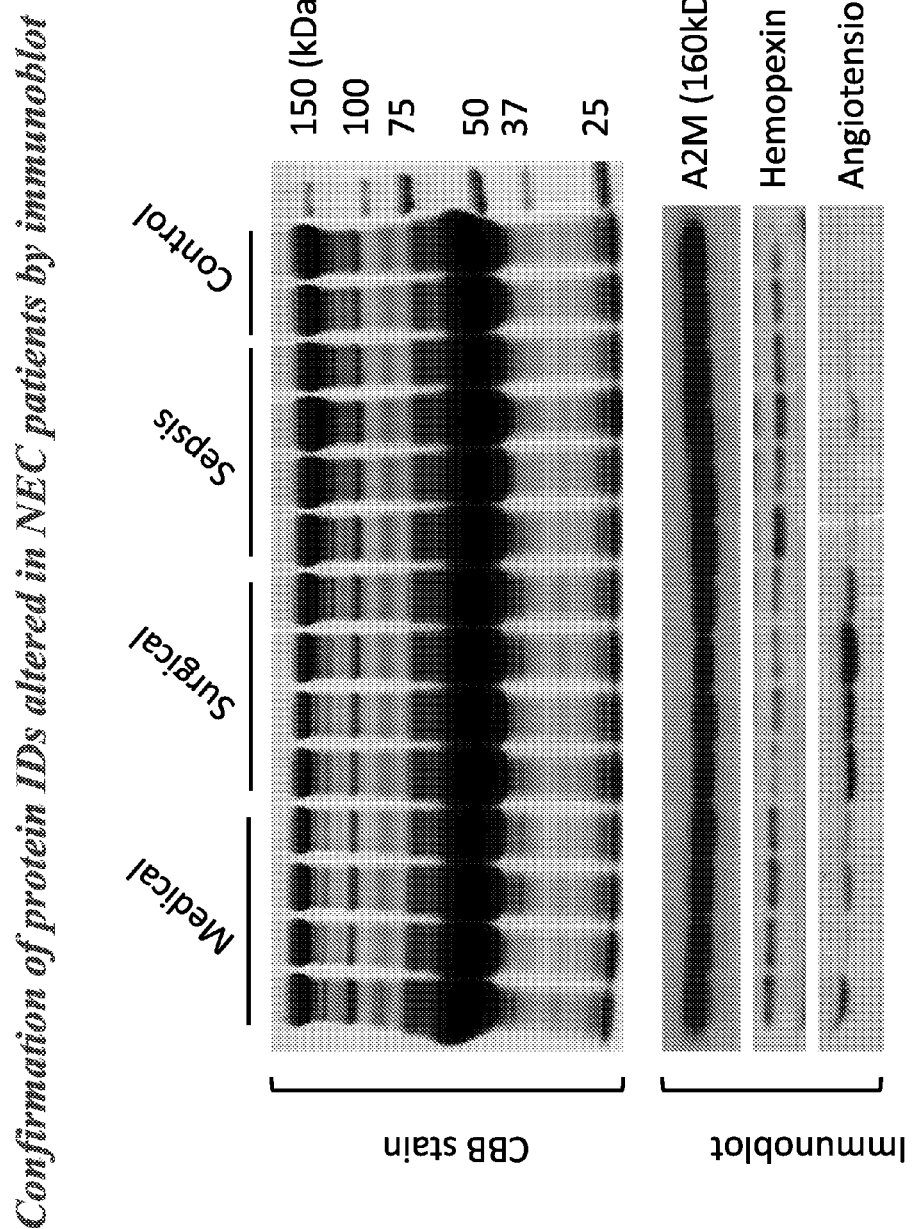
FIG. 3 illustrates the confirmation of proteins altered in NEC patients by immunoblot.
Figure 4:
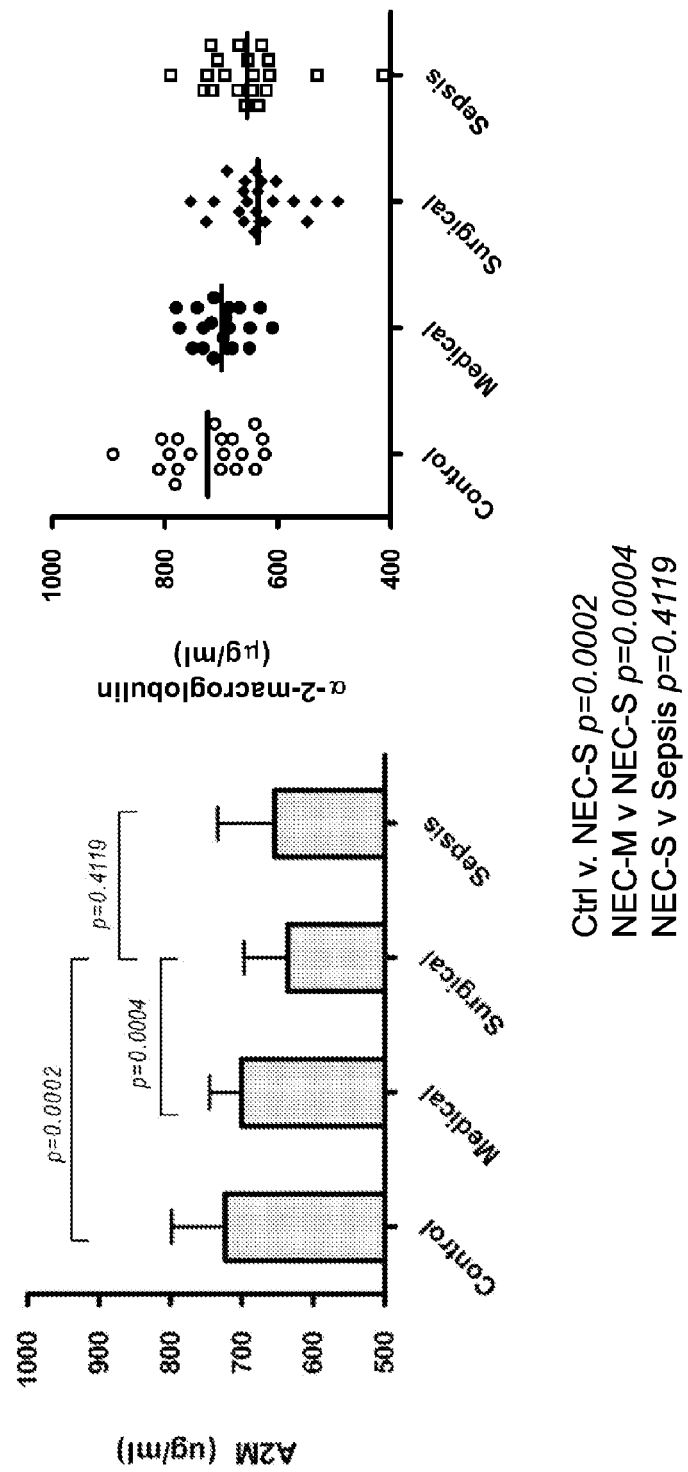
FIG. 4 depicts the validation of Alpha-2-macroglobulin (A2M) as an NEC-S-Dx biomarker (e.g., protein).
Figure 5:
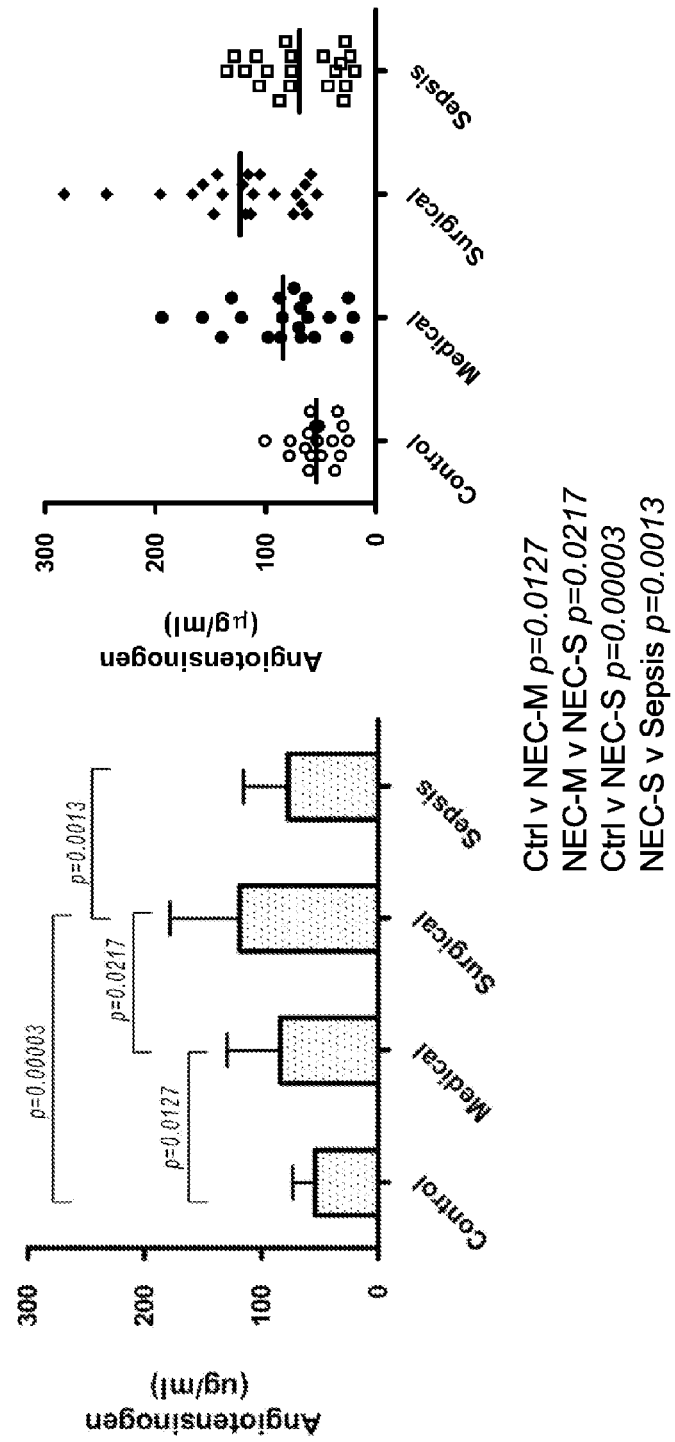
FIG. 5 depicts the validation of Angiotensinogen (AGT) as an NEC-S-Dx biomarker (e.g., protein).
Figure 6:
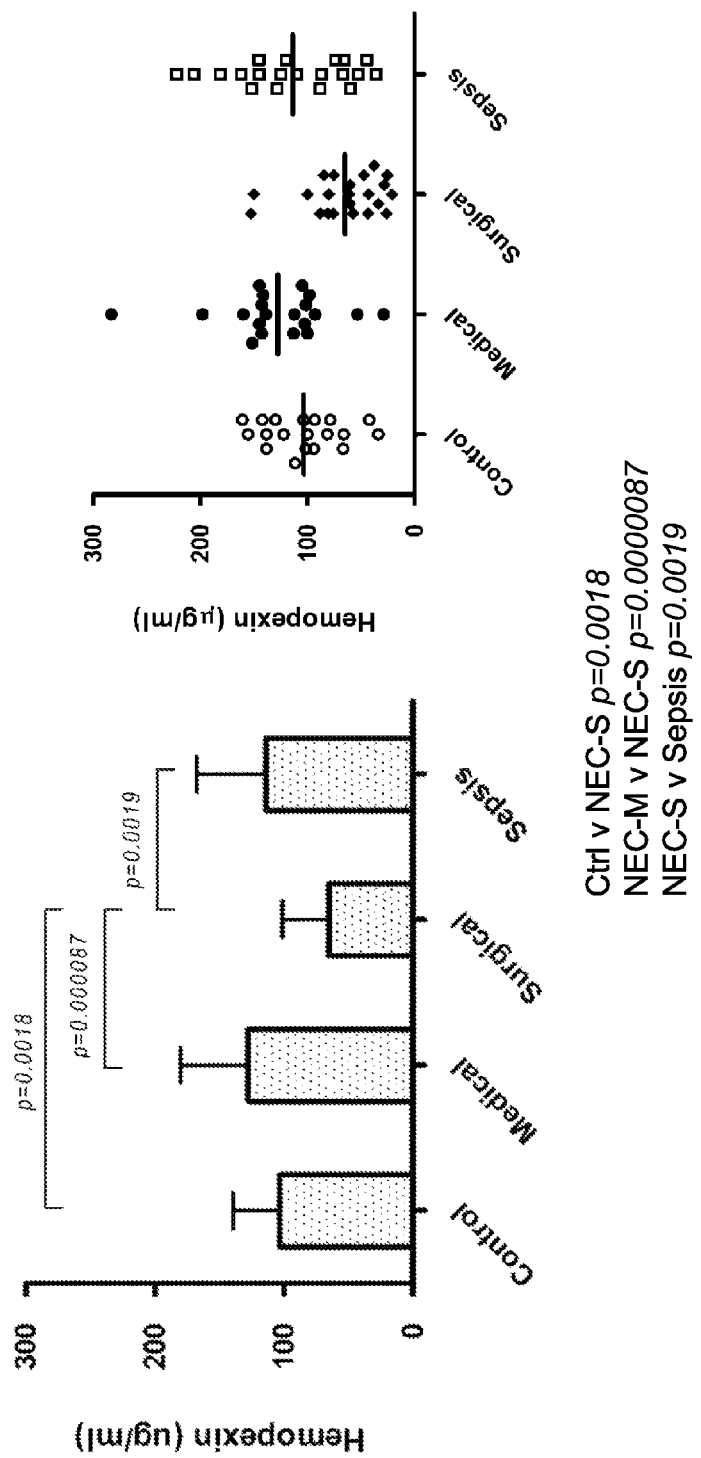
FIG. 6 depicts the validation of Hemopexin (HPX) as an NEC-S-Dx biomarker (e.g, protein).
Figure 9:
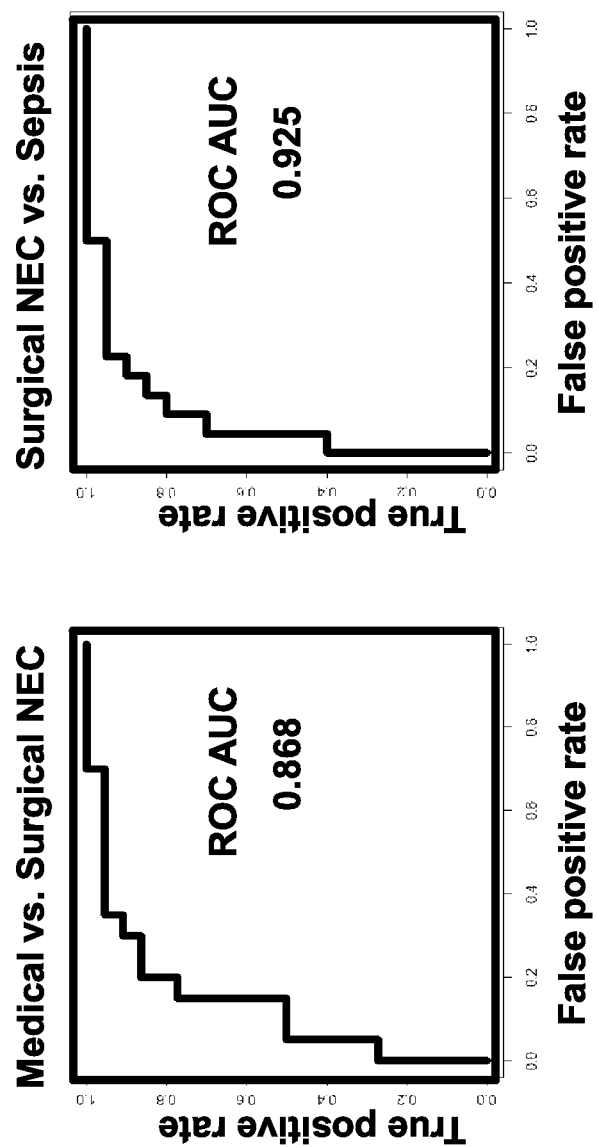
FIG. 9 depicts a ROC analysis (area under the curve-AUC) to compare False Positive rates with True Positive rates.
Figure 10:
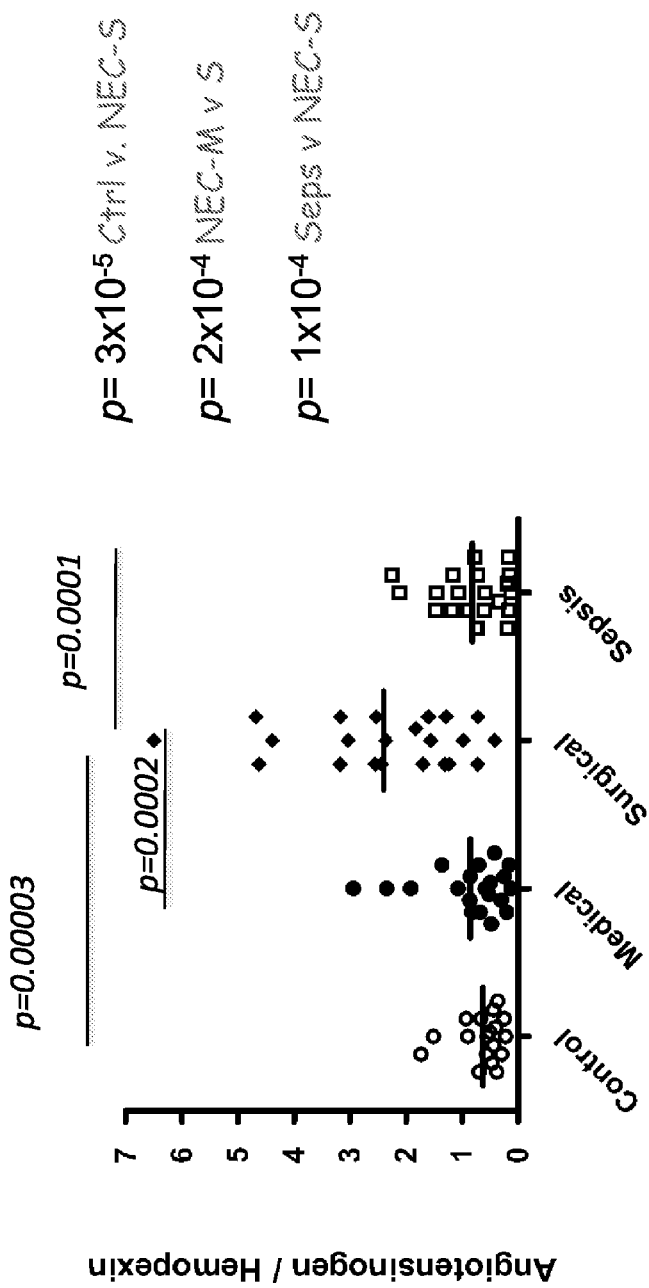
FIG. 10 shows that a ratio of AGT/HPX can be used as an integrated criteria for identifying a patient with NEC-S (e.g., to prognose an NEC, i.e. to determine whether a patient will be responsive to medical intervention or will require surgical treatment).

FIG. 1 depicts the study design for discovery of the potential biomarkers of NEC-S diagnosis. FIG. 2 presents the patient demographics of the patients used in the studies presented here. FIG. 3 illustrates the confirmation of protein IDs that were altered in NEC patients by immunoblot. FIGS. 4-6 and 10 depict that A2M, AGT, and HPX are NEC-S-Dx biomarkers. Levels of the encoded proteins were measured in blood samples from the indicated patient cohorts. FIG. 10 further shows that a ratio of AGT/HPX can be used as an integrated criteria for distinguishing a patient with NEC-S from a patient without NEC-S (i.e., to determine whether a patient has NEC-S or does not have NEC-S). FIG. 7 depicts the comparison of A2M, AGT, and HPX protein levels that were measured in normal, NEC-M, NEC-S, and sepsis patients. FIG. 8 presents the Mann Whitney test P values that were calculated for the measured protein levels in normal, NEC-M, NEC-S, and sepsis patients. FIG. 9 depicts a ROC analysis (area under the curve-AUC) that was performed to compare False Positive rates with True Positive rates.

Example 4

Figure 11:
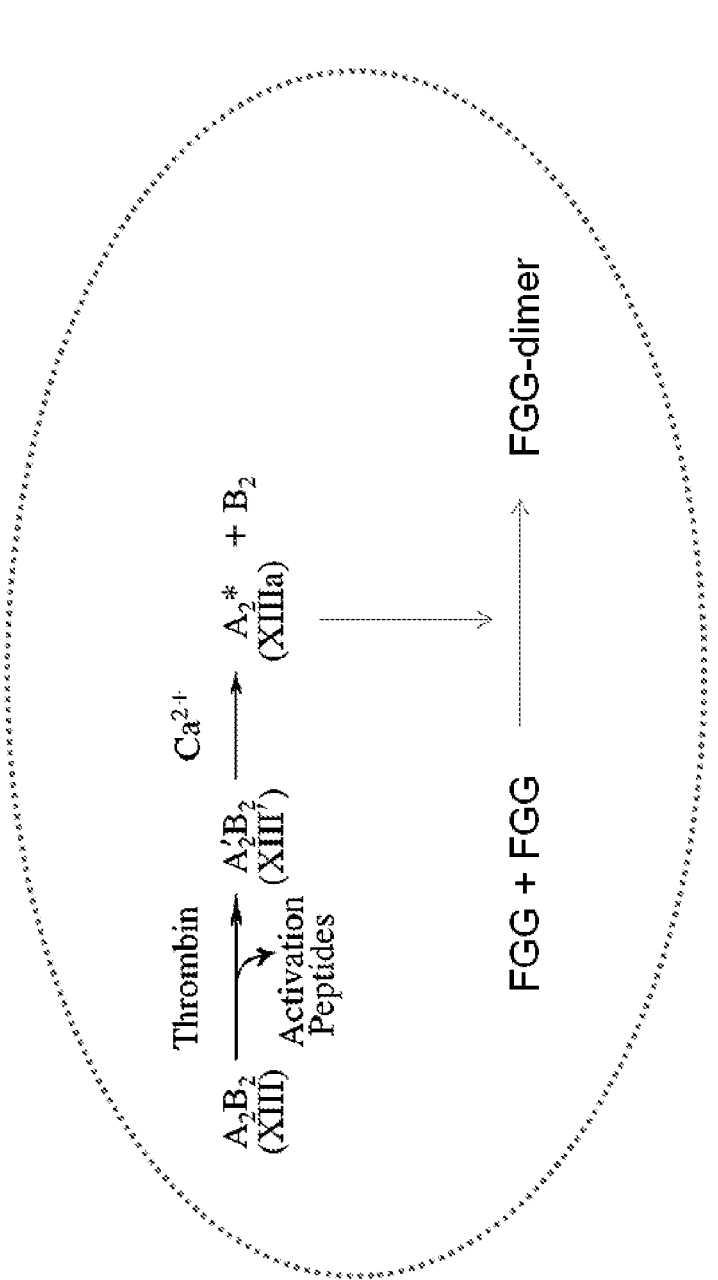
FIG. 11 schematically illustrates that dimer formation of Fibrinogen gamma chain (FGG) is catalyzed by Factor XIIIa (FXIIIa) transglutaminase activity.

Decreased Total Activity of FXIII in Human Plasma of Newborns with NEC Results in Failure to Form FGG Dimers FIG. 11 schematically illustrates that dimer formation of Fibrinogen gamma chain (FGG) is catalyzed by Factor XIIIa (FXIIIa) transglutaminase activity.

To assess FXIII changes in human plasma samples from infants with NEC, the following were measured: (1) in vivo FGG-dimer level (measured by immunoblot), which is produced by FXIIIa activity (FIG. 12); (2) total amount of factor XIII (FXIIIa+FXIII) (measured using quantitative sandwich ELISA) (FIG. 13); and (3) transglutaminase activity, as a measure of total FXIII activity (measured by assessing in vitro FGG-dimer formation (FIG. 14).

Plasma from NEC patients contained a decreased amount of FXIII as well as a decreased level of FXIII activity compared to plasma from sepsis or control patients.

FIG. 12 demonstrates that FGG dimers were significantly decreased in NEC plasma samples as compared to sepsis or control samples, and that the formation of FGG-dimers were induced by the addition of FXIIIa to pooled NEC samples. (A) Equal amounts of pooled plasma from indicated groups were separated on SDS-PAGE, followed by immunoblot using an FGG antibody. Note that FGG dimers, as indicated, were detected in sepsis and control plasmas, but not in medical or surgical NEC samples. (B) In vitro reconstitution of FGG-dimer in pooled NEC samples by addition of exogenous FXIIIa. Pooled NEC plasmas were incubated with (lane 2) or without (lane 1) CaCl2, thrombin and FXIII at RT for 10 min. Dimer formation was assessed by immunoblot using anti-FGG antibody. Note that the reconstitution of FGG dimer in NEC samples indicates low activity of FXIIIa in NEC plasma.

Figure 13:
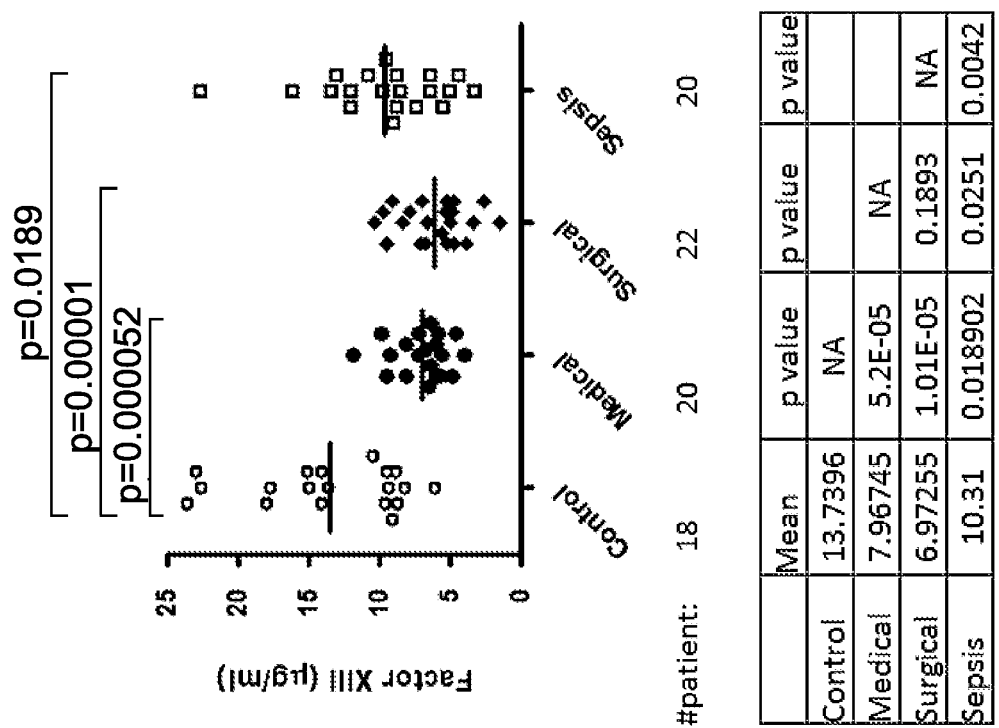
FIG. 13 demonstrates that the level of plasma FXIII in medical or surgical NEC is significantly lower than that in the control and the sepsis groups. This figure depicts the validation of FXIII protein level as an NEC-Dx biomarker.
Figure 14:
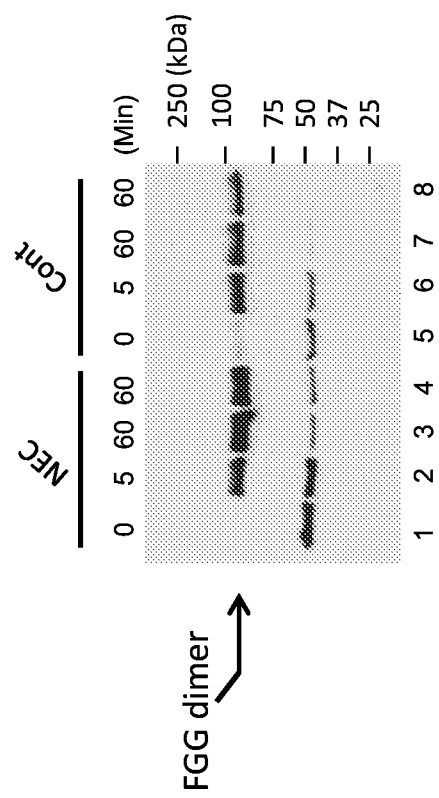
FIG. 14 demonstrates that the transglutaminase activity of FXIII is reduced in plasma isolated from NEC patients. This figure depicts the validation of FXIII activity level as an NEC-Dx biomarker.

FIG. 13 demonstrates that the level of plasma FXIII in medical or surgical NEC is significantly lower than that in the control and the sepsis groups. Quantitative measurement of FXIII was performed using sandwich ELISA kit to measure FXIII in plasma isolated from the indicated groups.

FIG. 14 demonstrates that the transglutaminase activity of FXIII is reduced in plasma isolated from NEC patients. The activity was assessed by measuring in vitro FGG-dimer formation after addition of FXIII activators. Pooled medical NEC and control plasmas were incubated with $CaCl_2$ and thrombin (FXIII activator) to activate FXIII at 25° C. (lanes 1-3, 5-7) or 37° C. (lanes 4, 8) for the indicated periods of time. FGG dimer formation was detected by immunoblot using FGG antibody. Note that the ratio of dimer vs. monomer was significantly lower in NEC as compared to control sample (lane 2 vs. 6), indicating that NEC plasma has less total activity of FXIII than control samples.

The preceding examples merely illustrate the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of obtaining a Necrotizing Enterocolitis (NEC) signature for a patient, the method comprising:
   (a) detecting in a blood sample from the patient the representation of one or more NEC biomarkers to obtain an NEC biomarker signature for the patient;
   (b) comparing the NEC biomarker signature from the patient to an NEC biomarker signature from a reference sample; and
   (c) making an NEC assessment for the patient based on the comparison, wherein the NEC assessment is at least one of:
      (i) an NEC diagnosis that consists of a determination of whether the patient has NEC, and
      (ii) a prediction of responsiveness to NEC medical intervention that consists of a determination of whether a patient having NEC will respond to medical intervention.

2. The method of claim 1, wherein the one or more NEC biomarkers are selected from the group consisting of Factor XIII (FXIII), Fibrinogen gamma chain (FGG) dimer, Angiotensinogen (AGT), Alpha-2-macroglobulin (A2M), and Hemopexin (HPX).

3. The method according to claim 1, wherein the representation of two NEC biomarkers are detected.

4. The method according to claim 1, wherein the NEC assessment is an NEC diagnosis and the one or more NEC biomarkers are selected from the group consisting of Factor XIII (FXIII) and Fibrinogen gamma chain (FGG) dimer.

5. The method according to claim 1, wherein the NEC assessment is a prediction of responsiveness to NEC medical intervention and the one or more NEC biomarkers are selected from the group consisting of: Angiotensinogen (AGT), Alpha-2-macroglobulin (A2M), and Hemopexin (HPX).

6. The method of claim 5, wherein the patient has been diagnosed as having NEC.

7. The method according to claim 1, wherein the NEC assessment is both an NEC diagnosis and a prediction of responsiveness to NEC medical intervention.

8. The method according to claim 1, further comprising obtaining an NEC clinical score for the patient, wherein the NEC assessment for the patient is made based on the comparison and on the NEC clinical score.

9. The method according to claim 1, wherein the patient is suspected of having NEC, intestinal perforation (IP), or sepsis.

10. The method of claim 1, wherein the NEC assessment is:
   (i) an NEC diagnosis based on one or more NEC biomarkers selected from the group consisting of Factor XIII (FXIII) and Fibrinogen gamma chain (FGG) dimer; and
   (ii) a prediction of responsiveness to NEC medical intervention based on one or more NEC biomarkers selected from the group consisting of: Angiotensinogen (AGT), Alpha-2-macroglobulin (A2M), and Hemopexin (HPX).

11. A method of treating a patient for Necrotizing Enterocolitis (NEC), the method comprising:
   (a) making an NEC assessment for the patient based on an NEC biomarker signature for a sample from a patient, wherein the NEC assessment is at least one of:
      (i) an NEC diagnosis that consists of a determination of whether the patient has NEC, and
      (ii) a prediction of responsiveness to NEC medical intervention that consists of a determination of whether a patient having NEC will respond to medical intervention; and
   (b) treating the patient based on the NEC assessment.

12. The method according to claim 11, further comprising a step of obtaining an NEC clinical score from the patient, wherein the NEC assessment for the patient further comprises considering the NEC clinical score.

13. The method according to claim 12, wherein, when the NEC assessment is a prediction of responsiveness to NEC medical intervention:
 (i) the treatment is surgery when the patient is predicted not to be responsive to NEC medical intervention; or
 (ii) the treatment is medical therapy comprising antibiotics and nothing by mouth when the patient is predicted to be responsive to NEC medical intervention.

14. The method according to claim 1, further comprising:
 (a) obtaining a blood sample from a patient suspected of having NEC; and
 (b) detecting in the blood sample from the patient the representation of one or more NEC biomarkers to obtain an NEC biomarker signature for the patient; and
 (c) comparing the NEC biomarker signature from the patient to an NEC biomarker signature from a reference sample; and
 (d) generating a report based on results from (c), wherein the report comprises an NEC assessment.

15. The method according to claim 14, wherein the NEC assessment indicates the likelihood of NEC in the patient.

16. The method according to claim 14, wherein the NEC assessment indicates the likelihood of responsiveness to NEC medical intervention.

17. The method according to claim 16, further comprising administering medical therapy comprising antibiotics and nothing by mouth to the patient when the NEC assessment indicates a high likelihood of responsiveness to NEC medical intervention.

18. The method according to claim 16, further comprising administering surgery to the patient when the NEC assessment indicates a low likelihood of responsiveness to NEC medical intervention.

19. The method according to claim 14, wherein the report further comprises an NEC clinical score comprising data on clinical findings regarding the patient.

* * * * *